United States Patent
Cohen et al.

(10) Patent No.: US 12,213,758 B2
(45) Date of Patent: Feb. 4, 2025

(54) ORIENTATION OF USER-INPUT DEVICES FOR CONTROLLING SURGICAL ARMS

(71) Applicant: MEMIC INNOVATIVE SURGERY LTD., Or-Yehuda (IL)

(72) Inventors: Dvir Cohen, Ramot-Menashe (IL); Yaron Levinson, Tel-Aviv (IL)

(73) Assignee: MOMENTIS SURGICAL LTD., Or Yehuda (IL)

( * ) Notice: Subject to any disclaimer, the term of this patent is extended or adjusted under 35 U.S.C. 154(b) by 220 days.

(21) Appl. No.: 17/782,153

(22) PCT Filed: Dec. 4, 2020

(86) PCT No.: PCT/IB2020/061508
§ 371 (c)(1),
(2) Date: Jun. 2, 2022

(87) PCT Pub. No.: WO2021/111394
PCT Pub. Date: Jun. 10, 2021

(65) Prior Publication Data
US 2023/0000579 A1    Jan. 5, 2023

Related U.S. Application Data

(60) Provisional application No. 62/944,351, filed on Dec. 5, 2019.

(51) Int. Cl.
*A61B 90/50* (2016.01)
*A61B 34/00* (2016.01)
(Continued)

(52) U.S. Cl.
CPC .............. *A61B 34/74* (2016.02); *A61B 34/30* (2016.02); *A61B 90/50* (2016.02);
(Continued)

(58) Field of Classification Search
CPC .......... A61B 34/74; A61B 34/30; A61B 90/50; A61B 2017/0046; A61B 2034/742; B25J 9/1689
See application file for complete search history.

(56) References Cited

U.S. PATENT DOCUMENTS

| | | |
|---|---|---|
| 6,723,106 B1 | 4/2004 | Charles |
| 7,766,821 B2 | 8/2010 | Brunnen |

(Continued)

FOREIGN PATENT DOCUMENTS

| | | |
|---|---|---|
| EP | 2130510 A1 | 12/2009 |
| JP | 2009107074 A | 5/2009 |
| WO | 2018/013965 A1 | 1/2018 |

OTHER PUBLICATIONS

International Search Report for PCT/IB2020/061506 document completed Mar. 17, 2021.
(Continued)

*Primary Examiner* — Kira Nguyen
(74) *Attorney, Agent, or Firm* — Marc Van Dyke; Momentum IP

(57) ABSTRACT

A surgical system comprises an articulated mechanical arm comprising arm segments connected serially by arm joints that flex and rotate, and first and second input-devices. The second input-device comprises a handle configurable to be oriented in any orientation in an x-y-z space, and the handle comprises segment members and joint members corresponding to the arm segments and arm joints of the arm. The arm joints can be actuatable by, and have the same degrees of freedom as, the handle joint member. A method of using the surgical system includes retroflecting the arm, transitioning control of the arm from the first input device to the second input device, and performing a surgical action, during which a displacement vector or a reorientation arc of the handle member through the x-y-z space is translated to a corre- (Continued)

sponding displacement vector or corresponding reorientation arc of the end effector in the same x-y-z space.

14 Claims, 19 Drawing Sheets

(51) Int. Cl.
  *A61B 34/30* (2016.01)
  *A61B 17/00* (2006.01)
(52) U.S. Cl.
  CPC ............... *A61B 2017/00017* (2013.01); *A61B 2017/00398* (2013.01); *A61B 2017/0046* (2013.01); *A61B 2034/742* (2016.02)

(56) References Cited

U.S. PATENT DOCUMENTS

| | | |
|---|---|---|
| 8,602,968 B2 | 12/2013 | Umemoto |
| 9,039,057 B2 | 5/2015 | Schvalb |
| 9,788,911 B2 | 10/2017 | Cohen |
| 9,820,822 B2 | 11/2017 | Cohen |
| 10,022,196 B2 | 7/2018 | Griffiths |
| 10,022,197 B2 | 7/2018 | Cohen |
| 10,052,165 B2 | 8/2018 | Cohen |
| 10,070,930 B2 | 9/2018 | Cohen |
| 10,188,472 B2 | 1/2019 | Diolaiti |
| 10,258,419 B2 | 4/2019 | Auld |
| 10,299,866 B2 | 5/2019 | Cohen |
| 10,470,831 B2 | 11/2019 | Cohen |
| 10,500,003 B2 | 12/2019 | Cohen |
| 10,617,481 B2 | 4/2020 | Cohen |
| 10,736,658 B2 | 8/2020 | Cohen |
| 10,849,654 B2 | 12/2020 | Cohen |
| 10,869,692 B2 | 12/2020 | Cohen |
| 10,973,592 B2 | 4/2021 | Cohen |
| 2007/0055103 A1 | 3/2007 | Hoefig |
| 2009/0247993 A1 | 10/2009 | Kirschenman |
| 2011/0313245 A1 | 12/2011 | Scholly |
| 2012/0059519 A1* | 3/2012 | Kishi ............... A61B 34/74 700/264 |
| 2012/0186383 A1 | 7/2012 | Schvalb |
| 2014/0088361 A1 | 3/2014 | Hrayr |
| 2015/0327940 A1 | 11/2015 | Inoue |
| 2016/0058269 A1* | 3/2016 | Komuro ............... A61B 1/0125 606/130 |
| 2016/0080701 A1 | 3/2016 | Henn |
| 2016/0135909 A1* | 5/2016 | Ogawa ............... B25J 3/04 606/130 |
| 2016/0135914 A1* | 5/2016 | Isoda ............... A61B 34/71 606/130 |
| 2016/0213435 A1 | 7/2016 | Hourtash |
| 2016/0242860 A1 | 8/2016 | Diolaiti |
| 2017/0071687 A1 | 3/2017 | Cohen |
| 2017/0071688 A1 | 3/2017 | Cohen |
| 2017/0079731 A1 | 3/2017 | Griffiths |
| 2017/0086932 A1 | 3/2017 | Auld |
| 2017/0112581 A1 | 4/2017 | Cohen |
| 2017/0112583 A1 | 4/2017 | Cohen |
| 2017/0119483 A1 | 5/2017 | Cohen |
| 2017/0135776 A1 | 5/2017 | Cohen |
| 2017/0231701 A1 | 8/2017 | Cohen |
| 2017/0239005 A1 | 8/2017 | Cohen |
| 2017/0258538 A1 | 9/2017 | Cohen |
| 2017/0258539 A1 | 9/2017 | Cohen |
| 2017/0334067 A1 | 11/2017 | Swarup |
| 2018/0256235 A1 | 9/2018 | Cohen |
| 2018/0256241 A1 | 9/2018 | Cohen |
| 2018/0256246 A1 | 9/2018 | Cohen |
| 2018/0256265 A1 | 9/2018 | Cohen |
| 2018/0256266 A1 | 9/2018 | Cohen |
| 2018/0256267 A1* | 9/2018 | Cohen ............... A61B 34/74 |
| 2018/0256268 A1 | 9/2018 | Cohen |
| 2019/0000574 A1 | 1/2019 | Cohen |
| 2019/0059868 A1 | 2/2019 | Cohen |
| 2019/0059939 A1 | 2/2019 | Cohen |
| 2019/0059940 A1 | 2/2019 | Cohen |
| 2019/0059941 A1 | 2/2019 | Cohen |
| 2019/0083193 A1 | 3/2019 | Cohen |
| 2019/0167363 A1 | 6/2019 | Cohen |
| 2019/0167364 A1 | 6/2019 | Cohen |
| 2019/0201147 A1 | 7/2019 | Kralicky |
| 2019/0231445 A1 | 8/2019 | Cohen |
| 2020/0289225 A1 | 9/2020 | Cohen |
| 2021/0059716 A1 | 3/2021 | Cohen |
| 2021/0196407 A1 | 7/2021 | Cohen |
| 2021/0236234 A1 | 8/2021 | Cohen |
| 2021/0338345 A1 | 11/2021 | Cohen |
| 2022/0054205 A1 | 2/2022 | Cohen |
| 2023/0000571 A1 | 1/2023 | Cohen |
| 2023/0000579 A1 | 1/2023 | Cohen |

OTHER PUBLICATIONS

International Search Report for PCT/IB2020/061508 document completed Mar. 24, 2021.
Written Opinion for PCT/IB2020/061506 document completed Mar. 17, 2021.
Written Opinion for PCT/IB2020/061508 document completed Mar. 24, 2021.

* cited by examiner

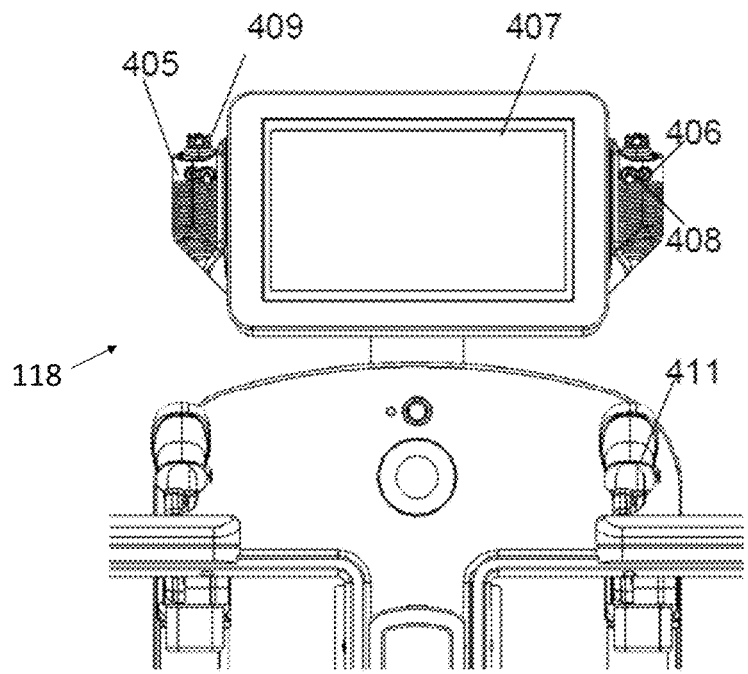
FIG. 7
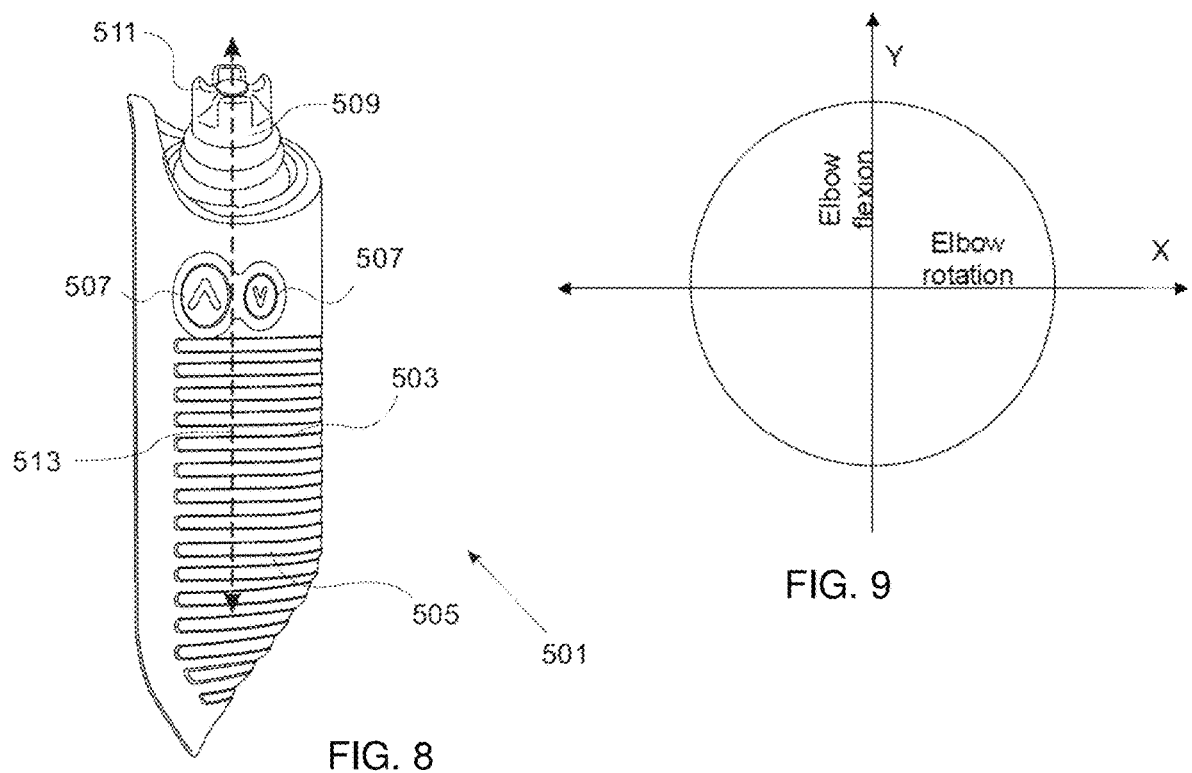
FIG. 8
FIG. 9

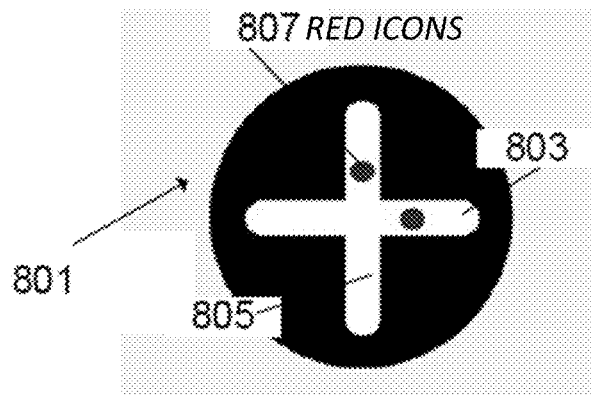
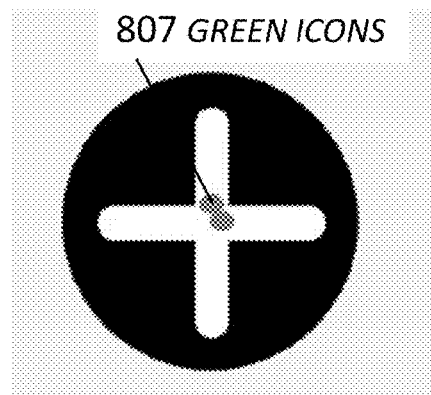
FIG. 12A  FIG. 12B
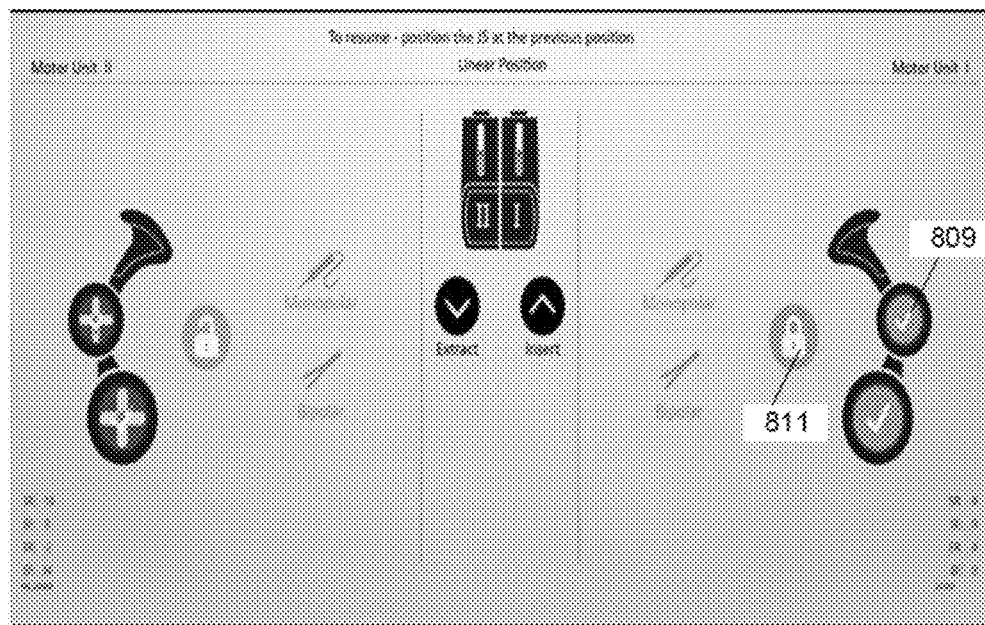
FIG. 13

Time = T1

Time = T2

ORIENTATION OF USER-INPUT DEVICES FOR CONTROLLING SURGICAL ARMS

CROSS-REFERENCE TO RELATED APPLICATIONS

This invention claims the benefit of U.S. Provisional Patent Application No. 62/944,351 filed on Dec. 5, 2019, which is incorporated herein by reference in its entirety.

FIELD OF THE INVENTION

The present invention relates to surgical systems used in performing surgery, and methods for using such systems, and particularly to controlling the bending and rotating of portions of articulated mechanical arms using multiple operating modes and input devices.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

It is well established that there are benefits of minimally invasive surgery. Instruments for such surgery typically have a surgical end effector located at the distal end of an articulated surgical arm (preferably with minimum diameter) that is inserted through a small opening (e.g., body wall incision, natural orifice) to reach a surgical site. In some instances, surgical instruments can be passed through a cannula and an endoscope can be used to provide images of the surgical site.

Surgical instruments have been developed that utilize an end effector (e.g., a surgical tool such as for tissue fusing or cutting, or a measurement tool) for convenience, accuracy, and wellbeing of the subject. In some cases, articulated surgical arms have one or more bending portions which are controlled remotely using various input devices (e.g., hand and foot controls) to ultimately control the location of the end effector and change its orientation with reference to the surgical arm's longitudinal axis. In some case, the surgical arm is capable of retroflected bending relative to the surgical arm longitudinal axis.

Clinical studies have demonstrated that the minimally invasive transvaginal approach to gynecological surgery is superior compared to the abdominal approach. Advantages include post-surgical recovery time, morbidity, infections, death rate, complications, blood loss and patient satisfaction. To this day, the policy of American College of Gynecology (ACOG) states that vaginal approaches to gynecological surgery are preferred whenever feasible. To enable a medical device entering trans-vaginally to perform gynecological surgery, articulated surgical arms are required to bend into a retroflected position.

The current state of the art is lacking devices and methods that can provide optimal control elements and methods of use to ensure that a preliminary retroflecting step is performed in a de-risked approach that does not affect the ergonomic comfort and convenience afforded by an input device optimized for arduous surgical procedures. Thus, there is a need for solutions which are suitable for restricting risk during retroflecting of surgical arms and provide maximal freedom of movement during surgical procedures while not impacting surgeon ergonomics.

SUMMARY OF THE INVENTION

A method is disclosed, of operating a surgical system, the surgical system comprising (i) an articulated mechanical arm having a surgical end effector at a distal end thereof, the arm comprising a plurality of arm segments connected serially by arm joints having respective degrees of freedom and configured to flex and rotate, and (ii) first and second input-devices, the second input-device comprising a handle member configured to be oriented in any one of a plurality of selectable orientations in an x-y-z space, the handle member comprising respective segment members and joint members that correspond, respectively, to the arm segments and arm joints of the arm, each of the respective arm joints actuatable by, and having the same degrees of freedom as, the corresponding joint member, the method comprising: (a) retroflecting the arm in response to an electronic control-output from the first input device, the electronic control-output being effective to regulate flexing and rotating of an arm joint so as to deliver the end effector to a retroflex operating position; (b) subsequent to the retroflecting of the arm, transitioning control of the arm from the first input device to the second input device; and (c) after the transitioning, performing a surgical action using the end effector by reorienting the handle member to displace and reorient, respectively, the segment members and joint members, thereby causing respective displacement and reorientation of the corresponding arm segments and arm joints of the retroflected arm, the orientation of the handle member being such that a displacement vector or a reorientation arc of the handle member through the x-y-z space is translated to a corresponding displacement vector or corresponding reorientation arc of the end effector in the same x-y-z space.

In some embodiments, carrying out the retroflecting step using the first input device may not include, i.e., may exclude, reorienting the handle member from a selected orientation in the x-y-z space. In some embodiments, carrying out the retroflecting step using the first input device may not require reorienting the handle member from a selected orientation in the x-y-z space. In some embodiments, carrying out the retroflecting step using the first input device may not require reorienting the handle member from a selected orientation in the x-y-z space by more than 90°.

In some embodiments, the surgical system can additionally comprise control circuitry effective to cause the transition.

In some embodiments, the first input device can be deactivated after the transition. In some embodiments, the first input device can be disconnected from the arm after the transition.

In some embodiments, the surgical system can comprise, or additionally comprise, a user-input device for actuating linear advancement and retraction of the arm. This user-input device can be an add-on, e.g., a button or nipple, on another user-input device.

According to embodiments of the invention, a surgical system for use with a surgical end effector comprises: (a) an articulated mechanical arm having a surgical end effector at a distal end thereof, the arm comprising a plurality of arm segments connected serially by arm joints having respective degrees of freedom and configured to flex and rotate; (b) a first input-device configured to deliver, in response to a change in position, an electronic control-output for controlling respective rates of flexing and rotating of an arm joint so as to retroflect the distal end of the arm and the end effector to a retroflex operating position; and (c) a second input-device comprising a handle member configured to be oriented in any one of a plurality of selectable orientations in an x-y-z space, the handle member comprising respective segment members and joint members that correspond, respectively, to the arm segments and arm joints of the arm, each of the respective arm joints actuatable by, and having the same degrees of freedom as, the corresponding joint member, wherein: (i) the surgical system is configured to be transitioned from controlling the arm with the first input device to controlling the arm with the second input device after the arm is retroflected, and (ii) following the transitioning, reorienting the handle member to displace and reorient, respectively, the segment members and joint members, is effective to cause respective displacement and reorientation of the corresponding arm segments and arm joints of the retroflected arm, and the orientation of the handle member is such that a displacement vector or a reorientation arc of the handle member through the x-y-z space is translated to a corresponding displacement vector or corresponding reorientation arc of the end effector in the same x-y-z space.

In some embodiments, carrying out the retroflecting using the first input device may not include, i.e., may exclude, reorienting the handle member from a selected orientation in the x-y-z space. In some embodiments, carrying out the retroflecting step using the first input device may not require reorienting the handle member from a selected orientation in the x-y-z space. In some embodiments, carrying out the retroflecting step using the first input device may not require reorienting the handle member from a selected orientation in the x-y-z space by more than 90°.

In some embodiments, the surgical system can additionally comprise control circuitry effective to cause the transition.

In some embodiments, the first input device can be configured to be deactivated after the transition. In some embodiments, the first input device can be configured to be disconnected from the arm after the transition.

In some embodiments, the surgical system can comprise a user-input device for actuating linear advancement and retraction of the arm.

A method is disclosed, according to embodiments, of operating a surgical system that comprises (i) an articulated mechanical arm having a surgical end effector at a distal end thereof, the arm comprising a plurality of arm joints having respective degrees of freedom, and (ii) an input-device array of one or more user-input devices configured to control flexing and rotating of arm joints, the method comprising: (a) in response to an electronic control-output from a first user-input device, retroflecting the distal end of the arm so as to deliver the end effector to a retroflex operating position, employing a first coordinate translation matrix to translate a user-input to a respective flexion and rotation of an arm joint; (b) in response to and contingent upon detecting that the end effector is in the retroflex operating position, transitioning to a second coordinate translation matrix that is based on the retroflex position of the end effector; and (c) after the transitioning and in response to an electronic control-output from a second user-input device, performing a surgical activity using the end effector, employing the second coordinate translation matrix to translate a user-input to a respective flexion and rotation of an arm joint.

In some embodiments, it can be that the first and second input devices are the same input device, and/or that the first and second coordinate translation matrices are not the same 3D-coordinate translation matrix.

In some embodiments, it can be that the first and second input devices are not the same input device, and/or that the first and second coordinate translation matrices are not the same 3D-coordinate translation matrix.

In some embodiments, it can be that before the transition and during the retroflecting, a proximal displacement of the first user-input device or a part thereof is translated to a proximal displacement of the end effector, and/or after the transition and with the end effector in the retroflex position, a proximal displacement of the second user-input device or a part thereof is translated to a distal displacement of the end effector.

In some embodiments, the surgical system can additionally comprise control circuitry effective to cause the transition.

In some embodiments, the first input device can be deactivated after the transition. In some embodiments, the first input device can be disconnected from the arm after the transition.

According to embodiments, a surgical system for use with a surgical end effector comprises: (a) an array of one or more input devices; and (b) an articulated mechanical arm having a surgical end effector at a distal end thereof, the arm comprising a plurality of arm segments connected by a plurality of arm joints configured to flex and rotate in response to a control signal generated by an input device, wherein the surgical system is configured to: (i) retroflect the distal end of the arm, in response to an electronic control-output from a first user-input device, so as to deliver the end effector to a retroflex operating position, employing a first coordinate translation matrix to translate the user inputs to respective flexions and rotations of an arm joint, (ii) transition to a second coordinate translation matrix that is based on a current orientation of the end effector, in response to and contingent upon a detection that said current orientation of the end effector corresponds to a current orientation of a second user-input device, and (iii) perform a surgical activity using the end effector after the transitioning and in response to an electronic control-output from the second user-input device, employing the second coordinate translation matrix to translate the user-inputs to respective flexions and rotation of an arm joint.

In some embodiments, it can be that the first and second input devices are the same input device, and/or that the first and second coordinate translation matrices are not the same 3D-coordinate translation matrix.

In some embodiments, it can be that the first and second input devices are not the same input device, and/or that the first and second coordinate translation matrices are not the same 3D-coordinate translation matrix.

In some embodiments, the surgical system can be configured such that before the transition and during the retroflecting, a proximal displacement of the first user-input device or a part thereof is translated to a proximal displacement of the end effector, and/or after the transition and with the end effector in the retroflex position, a proximal displacement of the second user-input device or a part thereof is translated to a distal displacement of the end effector.

In some embodiments, the surgical system can additionally comprise control circuitry effective to cause the transition.

In some embodiments, the first input device can be configured to be deactivated after the transition. In some embodiments, the first input device can be configured to be disconnected from the arm after the transition.

A method is disclosed, according to embodiments, of operating a surgical system comprising (i) a given user-input device and (ii) an articulated mechanical arm comprising a surgical end effector at a distal end thereof and a plurality of arm joints configured to flex and rotate in response to an electronic control-output from the given user-input device. The method comprises: (a) commencing operation of the surgical system in a first operating mode; (b) while the surgical system is in the first operating mode, (i) modifying a curve-shape of the arm by at least one of a mechanized flexion and a mechanized rotation of one or more of the arm joints of the articulated mechanical arm, and (ii) monitoring a shape-status of said mechanical arm to detect whether at least a portion thereof has a curve-shape that matches a currently-prevailing curve-shape defined by the given user-input device. The method additionally comprises: (c) in response to and contingent upon detecting that the curve-shape of the mechanical arm matches the curve-shape of the given user-input device, transitioning operation of the surgical system from the first mode to a second mode; and (d) operating the surgical system in the second mode such that an output of the given user-input device modifies a configuration of the arm or a section or element thereof so as to perform a surgical action using the end effector.

In some embodiments, the transitioning can comprise handing off user-control of a configuration of the arm from a user-input device that is not the given user-input device to the given user-input device.

In some embodiments, it can be that the first mode: (i) is defined with respect to a proper subset of the plurality of arm joints; (ii) precludes actuation, by control signals from the given user-input device, of any arm joints of the arm that is not a member of the proper subset of arm joints; and/or (iii) permits controlling the actuation of one or more arm joints belonging to the proper subset to cause a flexion of and/or a rotation of the one or more arm joints of the proper subset.

In some embodiments, it can be that upon transitioning from the first to the second mode, the given user-input device is enabled to control flexing and rotating of at least one first-mode-precluded arm joint.

In some embodiments, the modifying of the shape of the arm can be performed responsively to electronic control-signals provided by the given user-input device. In some embodiments, the modifying of the shape of arm can be performed responsively to electronic control-signals provided by a user-input device other than the given user-input device. In some embodiments, the modifying of the curve-shape of the arm can be performed automatically.

According to embodiments, a surgical system comprises (i) a given user-input device and (ii) an articulated mechanical arm comprising a surgical end effector at a distal end thereof and a plurality of arm joints configured to flex and rotate in response to an electronic control-output from the given user-input device. The system is configured to have operation commenced in a first operating mode, and during operation in the first operating mode to have curve-shape of the arm modified by at least one of a mechanized flexion and a mechanized rotation of one or more of the arm joints of the articulated mechanical arm. The system is further configured to have the shape-status of said mechanical arm monitored, to detect whether at least a portion thereof has a curve-shape that matches a currently-prevailing curve-shape defined by the given user-input device. The system is further configured such that in response to and contingent upon detecting that the curve-shape of the mechanical arm matches the curve-shape of the given user-input device, operation of the surgical system is transitioned from the first mode to a second mode, and to be operated in the second mode such that an output of the given user-input device modifies a configuration of the arm or a section or element thereof so as to perform a surgical action using the end effector.

In some embodiments, the system can be configured such that the transitioning can comprise handing off user-control of a configuration of the arm from a user-input device that is not the given user-input device to the given user-input device.

In some embodiments, the system can be configured such that the first mode: (i) is defined with respect to a proper subset of the plurality of arm joints; (ii) precludes actuation, by control signals from the given user-input device, of any arm joints of the arm that is not a member of the proper subset of arm joints; and/or (iii) permits controlling the actuation of one or more arm joints belonging to the proper subset to cause a flexion of and/or a rotation of the one or more arm joints of the proper subset.

In some embodiments, the system can be configured such that upon transitioning from the first to the second mode, the given user-input device is enabled to control flexing and rotating of at least one first-mode-precluded arm joint.

In some embodiments, the system can be configured such that the modifying of the shape of the arm can be performed responsively to electronic control-signals provided by the given user-input device. In some embodiments, the system can be configured such that the modifying of the shape of arm can be performed responsively to electronic control-signals provided by a user-input device other than the given user-input device. In some embodiments, the system can be configured such that the modifying of the curve-shape of the arm can be performed automatically.

A method is disclosed, according to embodiments, of operating a surgical system comprising (i) a given user-input device and (ii) an articulated mechanical arm comprising a surgical end effector at a distal end thereof and a plurality of arm joints configured to flex and rotate in response to an electronic control-output from the given user-input device. The method comprises: (a) commencing operation of the surgical system in a first operating mode; (b) while the surgical system is in the first operating mode, (i) modifying a curve-shape of the arm by at least one of a mechanized flexion and a mechanized rotation of one or more of the arm joints of the articulated mechanical arm, and (ii) monitoring a shape-status of said mechanical arm to detect whether at least a portion thereof has a curve-shape that matches a pre-defined curve shape. The method also comprises: (c) in response to and contingent upon detecting that the curve-shape of the mechanical arm matches the pre-defined curve shape, transitioning operation of the surgical system from the first mode to a second mode; and (d) operating the surgical system in the second mode such that an output of the given user-input device modifies a configuration of the arm or a section or element thereof so as to perform a surgical action using the end effector.

In some embodiments, it can be that detecting whether the curve-shape of the mechanical arm or of a portion thereof matches the pre-defined curve shape includes at least one of (i) detecting whether the curve-shape of the mechanical arm or a portion thereof matches a two-dimensional projection of the pre-defined curve shape, (ii) detecting whether a two-dimensional projection of the curve-shape of the mechanical arm or of a portion thereof matches the pre-defined curve-shape, and/or (iii) detecting whether a two-dimensional projection of the curve shape of the mechanical arm or of a portion thereof matches a two-dimensional projection of the pre-defined curve shape.

In some embodiments, the pre-defined curve shape can have one or more local minima or local maxima. In some embodiments, the pre-defined curve shape can have one or more inflection points. In some embodiments, the pre-defined curve-shape or a two-dimensional projection thereof can be an "S" curve-shape.

In some embodiments, the transitioning can comprise handing off user-control of a configuration of the arm from a user-input device that is not the given user-input device to the given user-input device.

In some embodiments, it can be that the first mode: (i) is defined with respect to a proper subset of the plurality of arm joints; (ii) precludes actuation, by control signals from the given user-input device, of any arm joints of the arm that is not a member of the proper subset of arm joints; and/or (iii) permits controlling the actuation of one or more arm joints belonging to the proper subset to cause a flexion of and/or a rotation of the one or more arm joints of the proper subset.

In some embodiments, upon transitioning from the first to the second mode, the given user-input device can be enabled to control flexing and rotating of at least one first-mode-precluded arm joint.

In some embodiments, the modifying of the shape of arm can be performed responsively to electronic control-signals provided by the given user-input device. In some embodiments, the modifying of the shape of arm can be performed responsively to electronic control-signals provided by a user-input device other than the given user-input device. In some embodiments, the modifying of the curve-shape of the arm is performed automatically.

According to embodiment, a surgical system comprises (i) a given user-input device and (ii) an articulated mechanical arm comprising a surgical end effector at a distal end thereof and a plurality of arm joints configured to flex and rotate in response to an electronic control-output from the given user-input device. The system is configured to be have operation commenced in a first operating mode, and while in the first operating mode, to have a curve-shape of the arm modified by at least one of a mechanized flexion and a mechanized rotation of one or more of the arm joints of the articulated mechanical arm, and to have a shape-status of said mechanical arm monitored to detect whether at least a portion thereof has a curve-shape that matches a pre-defined curve shape. The system is further comprised such that in response to and contingent upon detecting that the curve-shape of the mechanical arm matches the pre-defined curve shape, operation of the surgical system is transitioned from the first mode to a second mode; and (d) the surgical system is configured to be operated in the second mode such that an output of the given user-input device modifies a configuration of the arm or a section or element thereof so as to perform a surgical action using the end effector.

In some embodiments, the system can be configured such that detecting whether the curve-shape of the mechanical arm or of a portion thereof matches the pre-defined curve shape includes at least one of (i) detecting whether the curve-shape of the mechanical arm or a portion thereof matches a two-dimensional projection of the pre-defined curve shape, (ii) detecting whether a two-dimensional projection of the curve-shape of the mechanical arm or of a portion thereof matches the pre-defined curve-shape, and/or (iii) detecting whether a two-dimensional projection of the curve shape of the mechanical arm or of a portion thereof matches a two-dimensional projection of the pre-defined curve shape.

In some embodiments, the system can be configured such that the pre-defined curve shape can have one or more local minima or local maxima. In some embodiments, the system can be configured such that the pre-defined curve shape can have one or more inflection points. In some embodiments, the system can be configured such that the pre-defined curve-shape or a two-dimensional projection thereof can be an "S" curve-shape.

In some embodiments, the system can be configured such that the transitioning can comprise handing off user-control of a configuration of the arm from a user-input device that is not the given user-input device to the given user-input device.

In some embodiments, the system can be configured such that the first mode: (i) is defined with respect to a proper subset of the plurality of arm joints; (ii) precludes actuation, by control signals from the given user-input device, of any arm joints of the arm that is not a member of the proper subset of arm joints; and/or (iii) permits controlling the actuation of one or more arm joints belonging to the proper subset to cause a flexion of and/or a rotation of the one or more arm joints of the proper subset.

In some embodiments, the system can be configured such that upon transitioning from the first to the second mode, the given user-input device can be enabled to control flexing and rotating of at least one first-mode-precluded arm joint.

In some embodiments, the system can be configured such that the modifying of the shape of arm can be performed responsively to electronic control-signals provided by the given user-input device. In some embodiments, the system can be configured such that the modifying of the shape of arm can be performed responsively to electronic control-signals provided by a user-input device other than the given user-input device. In some embodiments, the system can be configured such that the modifying of the curve-shape of the arm is performed automatically.

BRIEF DESCRIPTION OF THE DRAWINGS

The invention will now be described further, by way of example, with reference to the accompanying drawings, in which the dimensions of components and features shown in the figures are chosen for convenience and clarity of presentation and not necessarily to scale. In the drawings:

FIG. 7 is a schematic illustration of a control console for a surgical system with input devices positioned in proximity thereto, according to embodiments of the present invention.

FIG. 8 is a schematic illustration of a user-input device according to embodiments of the present invention.

FIG. 9 is a chart illustrating an exemplary scheme for using an input-device to control flexion and rotation of an arm joint, according to embodiments of the present invention.

FIGS. 12A-B illustrate an exemplary graphical aid for use in aligning the respective positions of a mechanical surgical arm and an articulated user-input device, according to embodiments of the present invention.

FIG. 13 shows a sample screen display for use in aligning the respective positions of a mechanical surgical arm and an articulated user-input device, according to embodiments of the present invention.

DETAILED DESCRIPTION OF EMBODIMENTS

Figure 1:
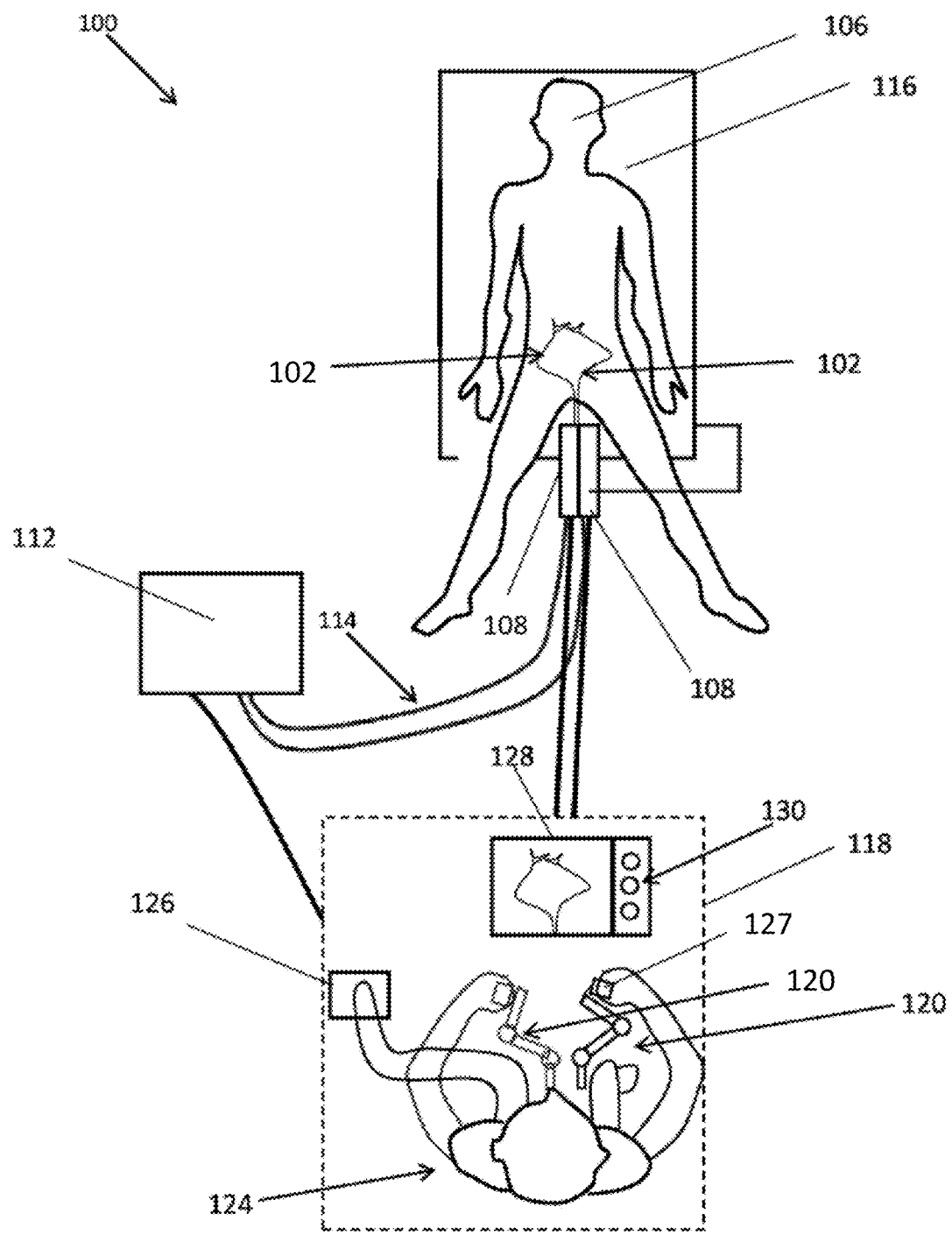
FIG. 1 is a schematic illustration of a surgical system according to embodiments of the present invention.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are generally used to designate like elements.

Embodiments disclosed herein relate to controlling one or more surgical mechanical arms, i.e., articulated mechanical arms, using a plurality of different operating modes and/or a plurality of different input devices.

Whenever 'arm' is used herein or in the appended claims, it means an articulated, mechanical arm that is part of a surgical system or electrosurgical system and used for performing or helping to perform surgical (including electrosurgical) actions inside a human subject's body. 'Surgical actions' when unspecified can include any medical or surgery-related or diagnostic action taken inside the human body, including, but not exhaustively: cutting tissue, dissecting tissue, manipulating tissue, suturing tissue, retracting tissue, fusing tissue, taking measurements, and imaging. It can be desirable that a surgical arm be sized and/or shaped for insertion into a human body. For example, an arm can be sized and/or shaped for insertion through a laparoscopic port and/or for performing laparoscopic surgery. For example, an arm can be sized and/or shaped for insertion through a natural body orifice, e.g. vagina, anus, trachea, esophagus, ear canal.

An arm may include an end effector, which is used herein to mean a tool or device used in connection with surgery, electrosurgery, diagnosis or imaging when deployed within a human body. An end effector may be supplied as part of an arm, i.e., already mounted, mechanical attached and/or integrated with the power and communications conveyances of the arm; in some embodiments an arm an end effector may be provided separately for assembly and/or integration into a working unit before or even during a surgical operation, i.e., before insertion into a subject's body. In any case, terms such as 'an arm comprising an end effector' and 'and arm configured for use with an end effector', etc., should be understood as equivalent for the purposes of this disclosure and the claims appended thereto.

An 'input device', or, equivalently, a 'user-input device', as used herein can be any device capable of receiving a user input, i.e., an input received from a user of a surgical system. Input devices can include, for example but not exhaustively: buttons, switches, toggles, wheels, knobs, small sticks such as thumbsticks (alternatively called nipples), and joysticks (whether articulated or not). Disclosure of specific device-type for any specific input device is not intended to exclude the substitution of other types of input devices for the specific input devices. Input devices can be standalone, grouped on a single control member or on a small number of control members, disposed upon another input device, or co-located, e.g., on or in proximity to a control console, display screen, etc. Input devices can be operated by a user employing one or more fingers, thumbs, hands or feet. Additionally or alternatively, and without limitation, input devices can be eye- or hand-motion operated, voice-operated, or controlled by facial expressions.

Arms and input devices, as well as other aspects and features of the present invention may be understood in combination with any of the teachings of co-pending U.S. patent application Ser. No. 16/121,704 filed on Sep. 5, 2018 and published as US Patent Publication US20190000574A1 which is hereby incorporated by reference herein in its entirety.

A 'handle', or, equivalently a 'handle-member', is used herein generally to describe a hand-operated user-input device or a hand-operated portion of a user-input device, and in some embodiments to describe a hand-grasped or finger-grasped user-input device or portion thereof. Drawings and accompanying descriptions of handles and hand-operated user-input devices in this disclosure are provided as illustrative examples, and such drawings and accompanying descriptions are not to be understood as limiting the scope of the embodiments as pertains to handle/handle-member design, connectivity and functionality.

For the present disclosure, 'module' and/or 'electrical circuitry' or 'electronic circuitry' and/or control circuitry' and/or element and/or unit and/or controller and/or module and/or sensor and/or detector may include any combination of analog and/or digital circuitry and/or software/computer readable code module and/or firmware and/or hardware elements including but not limited to a digital computer, CPU, volatile or non-volatile memory, field programmable logic array (FPLA) elements, hard-wired logic elements, field programmable gate array (FPGA) elements, and application-specific integrated circuit (ASIC) elements. Any instruction set architecture may be used including but not limited to reduced instruction set computer (RISC) architecture and/or complex instruction set computer (CISC) architecture.

In different embodiments, any computation or analysis procedure may be performed using any combination of analog and/or digital circuitry and/or software/computer readable code module and/or firmware and/or hardware elements including but not limited to a digital computer, CPU, volatile or non-volatile memory, field programmable logic array (FPLA) elements, hard-wired logic elements, field programmable gate array (FPGA) elements, and application-specific integrated circuit (ASIC) elements. Any instruction set architecture may be used including but not limited to reduced instruction set computer (RISC) architecture and/or complex instruction set computer (CISC) architecture.

Referring now to the figures, FIG. 1 shows a schematic illustration of a surgical system 100 according to embodiments. The system 100 of FIG. 1 includes two surgical mechanical arms 102. In other examples of a surgical system, a single surgical arm is provided. In other examples, more than two (e.g., 3 or 4) surgical arms are provided. Surgical mechanical arms 102 are preferably sized and/or shaped for insertion into a human body or patient 106. Each of the surgical mechanical arms 102 is actuated by a respective motor unit 108. The surgical arms 102 and/or motor units 108 are supported in this simplified illustrative example by attachment to a patient support 116, e.g., a bed, but may also be supported by a patient side cart or any other suitable equipment.

Power to the arms 102 and the motor units 108 can supplied by an electrosurgical generator 112 in embodiments in which the surgical system is used in electrosurgery. As known in the art of electrosurgery, an electrosurgical generator supplies high-frequency (e.g. radio frequency) alternating polarity, electric current. An electrosurgical generator 112 can be configured to supply different frequencies and/or power levels, for example, suitable for cutting and/or coagulating and/or sealing and/or desiccating and/or fulgurating tissue. Power is supplied to the motor units 108 via one or more cables 114 which are configured to transfer radio frequency electrosurgical power.

Movement of the surgical arms 102 is controlled at a control console 118. Movement is in response to signals generated by one or more input devices. Control console 118 includes a plurality of user interfaces including one or more of: input devices, e.g., input device arms 120 where the control console is configured to generate control signals based upon movement of the input device arms 120; display screen 128 configured to receive user input and/or display, for example, system-status information or imaging of a surgical zone, for example, to display images collected by a camera inserted into patient 106 using one of surgical arms 102 or display arm position and orientation; and one or more additional user interfaces 130 (e.g. button, switch, etc.).

Control console 118 includes a processor (not shown) configured to receive signals from a user input/s and to send control signals to motor units 108 and/or electrosurgical generator 112. Foot pedal 126 and/or electrosurgical generator 112 include/s a processor (not shown) configured to receive control signals (e.g. generated by a user pressing on a portion/s of the foot pedal 126) to vary electrical power supplied to motor units 108 based on the control signals. Foot pedal control signals do not necessarily pass through a control unit processor.

As will be explained in greater detail hereinbelow, in one control mode, the movement of input device arms 120 controls movement of a respective surgical device arm 102. A user 124 can position and/or move an input arm 120 by grasping an input device arm handle 127. Input arms are one form of input device, and are shown here for illustrative purposes. In other embodiments, other types or forms of input devices can be used.

Figure 2A:
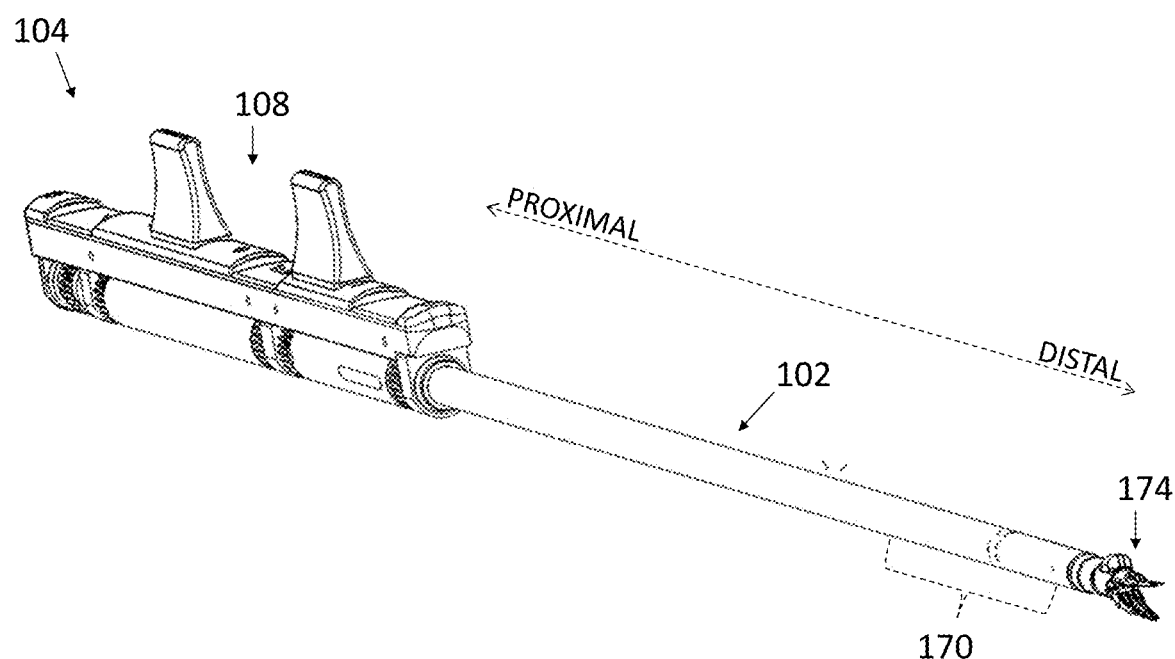
FIG. 2A is a schematic perspective view of a surgical system comprising a mechanical surgical arm according to embodiments of the present invention.
Figure 2B:
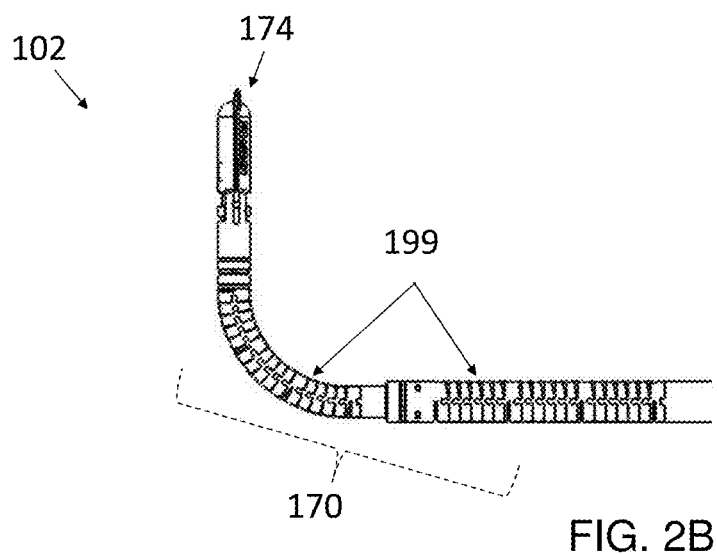
FIG. 2B shows a distal portion of a mechanical surgical arm according to embodiments of the present invention.

Referring now to FIGS. 2A-B, an arm unit 104 includes a proximal end which is shaped for acceptance by the motor unit 108, and a distal end where an end effector 174 such as the illustrated multi-jaw grasper (shown only as a non-limiting illustrative example) is attached to the arm 102.

The use of the relative terms 'proximal' and distal are in accordance with the arrows shown in FIG. 2A and are used in this manner throughout this disclosure and the appended claims: as shown, the distal end of the arm 102 at which the end effector 174 is disposed is the end furthest removed from the motor unit 108 and which is the first portion of the arm to be inserted in a human subject 19. The proximal end, therefore, is the end opposite the distal end, closest to the motor unit 108. The term 'distal portion' as used herein means any portion of the arm 102 which includes the distal end/tip (optionally including the end effector 174) and less than half the length of the arm 102. In FIG. 2B, a bendable portion 170 of the arm 102, i.e., a portion that contains one or more bendable joints, is located along the length of the arm, closer to the distal end. The bendable portion 170 can comprise a series of 'stacked links' 199 that enable flexibility for the outer contour/surface of the arm 102; an example of a plurality of stacked links 199 in a bendable portion 170 of an arm 102 is illustrated in FIG. 2B.

As used herein, an 'operating mode' or its equivalent 'mode' (which can be used in conjunction with various non-limiting descriptive words, e.g., 'retroflexing mode', 'surgical-operating mode,' etc.) means an operating regime imposed on the use of a surgical system or an arm, either by hardware, firmware or software design or by control circuitry of the surgical system or in other ways. To clarify: The word 'operating' in 'operating mode' means 'working' or 'functioning/al' and describes the operating of, e.g., an arm, and does not mean the performance of surgery, i.e., an 'operating mode' may happen to include the performance of surgery but not necessarily. The imposed operating regime can include, and not exhaustively, restricting or not restricting certain actions or certain portions of the surgical system that perform one or more actions, and the restricting or not restricting can include and/or can be equivalent to enabling or disabling, locking or unlocking, and precluding or permitting or similar words and phrases. In some embodiments herein, a mode is dedicated or directed to accomplishing a single goal, for example retroflecting a distal portion of an arm, and may be limited to one or more specific time periods. In other embodiments, a mode can incorporate an unlimited number of goals and actions and unlimited or undefined time periods.

Operation of the surgical system can be differentiated between different modes, in various ways, as further described hereinbelow. For example, the differentiation can be on the basis of (and not exhaustively): having a different input device (or multiple input devices) dedicated to each mode; having various restrictions or limitations on specific arm movements and/or on specific arm joints and segments; having different translation schemes for displacement of input devices or control elements of input devices to arm movements, e.g., displacement-to-speed vs. displacement-to-displacement, whether the translation from user inputs to arm movements is robotic/semi-autonomous or tele-operated; and whether the manipulation of the input device addresses (via the mechanics and electronics of the surgical system) the flexing and rotating of arm joints directly, or indirectly by addressing the displacements of arm segments which in turn causes the necessary flexions and rotations to occur in order to displace the arm segments as directed. The differentiations can be used in combination, and they can vary from arm to arm in a multi-arm system. In some embodiments, the differentiations can change while the system is in a given mode.

Some differentiations between modes can be implemented in more than one way. As a non-limiting example, if the differentiation between modes involves restricting or limiting certain arm movements (e.g., flexing and rotating of certain joints) or permitting only certain arm movements, the differentiation can be implemented by using different input devices for each mode, or by using one input device in both modes but enforcing, on the one input device, a software or hardware restriction that can be user-switchable or system-enforced. Regardless of whether an embodiment calls for one input device or more, a software-implemented or hardware-implemented solution may actively permit the actuation of a single given arm joint, or may actively prevent or preclude the actuation of any arm joint (of the same arm) that is not the single arm joint.

It should be noted that wherever actuation or movement of a singular 'arm' (as opposed to the plural 'arms' is discussed herein, this is for convenience only and is not intended to indicate whether or not a second arm (or other multiple arms) is/are being likewise or otherwise actuated or moved. Each arm can be controlled and actuated independently of any other arms by a respective input device. On the other hand, wherever an 'arm' (singular) is disclosed as being restricted or limited as to actuation or movement, e.g., when in an operating mode characterized by such a limitation or restriction, the limitation or restriction may apply equally to both/all arms of a surgical system. In some embodiments, however, a restriction or limitation may apply to one or more given arms while other arms are not restricted or limited at all, or not restricted or limited in the same way.

In embodiments in which two different operating modes are employed, a first operating mode is typically used when introducing or exiting and/or navigating the surgical arm or arms into or out of the body (or from a first point to a second point within the body) and more specifically towards or away from a target surgical site. The second operating mode is typically used when performing surgical actions (e.g. dissecting tissue, manipulating tissue, suturing tissue, taking measurements, imaging, etc.). The 'navigating' of the first mode may include retroflexing the arm or arms so as to put at least a portion of the arm or a distal portion thereof in a retroflex position or, equivalently, to put an end effector in a retroflex operating position (working position).

It can be desirable to have a clearly defined transition or 'handoff' from one operating mode to another. In some embodiments, the transition includes a handoff from one input device (or plurality of input devices) to another. In other embodiments, the transition is entirely concerned with changing control aspects that are differentiated between one mode and another wherein the tasks assigned to both modes can be accomplished by a single input device, or by the same input devices. A transition can be initiated and managed by the surgical system, or it can be initiated by a user.

In a non-limiting example with respect to a transition from a first mode to a second mode, a transition may include ending restrictions or limitations imposed during first-mode operation, such as limiting joint flexion and rotation to a given single arm joint of any particular arm, e.g. the elbow joint. Additionally or alternatively, a transition can include enabling the actuation of arm joints that were disabled (or not specifically enabled) in the first-mode operation, i.e., in addition to the single given joint that was enabled in the first mode. Enablement can include enablement of joints to move unrestrictedly in accordance with respective degrees of freedom of each joint. For example, if a given arm joint is only configured for rotation and not flexion, the enablement will enable it only for rotation. Additionally or alternatively, a transition can enable actuation of all arm joints. Additionally or alternatively, a transition can change a processing of control-outputs from user-input devices from a displacement-to-velocity translation to a displacement-to-displacement translation. In further non-limiting examples, the transition can be implemented automatically by control circuitry in response to an event, it can be implemented based on a user input such as, for example, a depressed button or a rotated switch, or it can be implanted by noting that a user has ceased using a first input device and begun using a second input device. In a further non-limiting example, the transition is a user interface-based mediated transitioning.

In a non-limiting example with respect to a transition from a second mode to a first mode, a transition may include restoring restrictions or limitations removed during a transition to second-mode operation, such as limiting joint flexion and rotation to a given single arm joint of any particular arm, e.g. the elbow joint. Additionally or alternatively, a transition can include disabling the actuation of arm joints that were enabled for the second-mode operation. Additionally or alternatively, a transition can change back a processing of control-outputs from user-input devices from a displacement-to-displacement translation to a displacement-to-velocity translation. In further non-limiting examples, the transition can be implemented based on a user input such as, for example, a depressed button or a rotated switch, or it can be implanted by noting that a user has ceased using an input device dedicated to second-mode operation and begun using a different input device that is dedicated to first-mode operation.

In embodiments, and especially in embodiments in which the input device employed in the second mode is avatar-like and translates input arm displacements to surgical arm displacements, transitioning from a first operating mode to a second operating mode can include an alignment calibration. In an alignment calibration, which is discussed in further detail with respect to FIGS. 12A-12B, the orientation of the surgical arm, including the 'internal' orientation of arm elements (e.g., arm joints and/or arm segments) with respect to each other is modified so as to match a 'shape' or 'curve' which describes the corresponding orientation of the input arm which will take over actuation control of the surgical arm in the transition to the second operating mode. There is not necessarily a corresponding alignment calibration in the case of transitioning back from the second operating to the first operating mode.

Translation of user inputs to arm movements (flexion and rotation) can be accomplished in various ways. For example, the displacement (or the force of displacement) of an input device or of a control element of an input device can be translated to a velocity (e.g., velocity, speed, angular velocity) of arm movement. It can be desirable in a first mode that includes insertion/extraction and retroflexing (or retroflexing/unflexing) to use this type of translation. These limited and, in some embodiments, less precise, movements can be conducive to being performed not in a tele-operated or avatar mode but to simpler robotic or semi-autonomous mode. In contrast, the movements required in a second mode dedicated to performing various surgical actions may be more conducive to a controlled displacement-displacement translation, where displacement of an input device or a control element of an input device is suitably translated to displacement of arm segments and indirectly to rotation and flexing of joints. For example, in the second more, it can be desirable to ensure that the articulation of an articulatable input device corresponds in internal orientation (i.e., segment-to-segment orientation) to the surgical arm, so that the translation of displacement to displacement is more intuitive, ergonomic and precise.

It can be desirable, in a first mode, to restrict arm movements to flexing and/or rotating a single given arm joint of an arm (or of each arm). This can be suitably implemented by configuring the surgical system to receive, from the input device used in the first mode, inputs which directly address the flexing and rotating of specific arm joints such as the single given arm joint that is permitted (in the operating mode) to be actuated. In other words, the user is 'controlling', via the input device and suitable control circuitry, the arm joint itself. The movement intended to be actuated in this case is specifically a flexion and/or rotation of the arm joint. Regardless of whether the actual arm movements are performed semi-autonomously in response to the user's control inputs, the user understands that she is controlling the actuation of the joint. The attending displacement and reorientation of the end effector is a presumably intended consequence of the control of the joint.

In contrast, it can be desirable, in a second mode, and especially in embodiments in which the input device employed in the second mode is avatar-like and translates input arm displacements to surgical arm displacements, for the surgical system to receive and process inputs which directly address the displacement of arm segments. The flexing and rotating of arm joints are then indirectly addressed by the surgical system by controlling the arm joints to flex and rotate to the extent necessary for achieving the required arm segment displacement and reorientation. In other words, the user is 'controlling' the displacement and reorientation of arm segments (or of the end effector which for the purpose of this discussion plays a role similar to that of any arm segment in that controlling its position and orientation is a user goal), and the control circuitry of the surgical system uses this information to determine the necessary flexion and rotation of each affected arm joint. In an embodiment, an avatar-like input arm can be manipulated by a user into a shape or configuration that anticipates or drives the intended shape of the surgical arm post-manipulation.

In an exemplary first operating mode, surgical arm movement can be at least partially limited or restricted, and certain types of movements can be precluded while others are permitted. For clarity, 'movement' of an arm can include displacement and/or reorientation of any portion of the arm, such as, for example, one or more segment members of the arm.

Figure 3A:
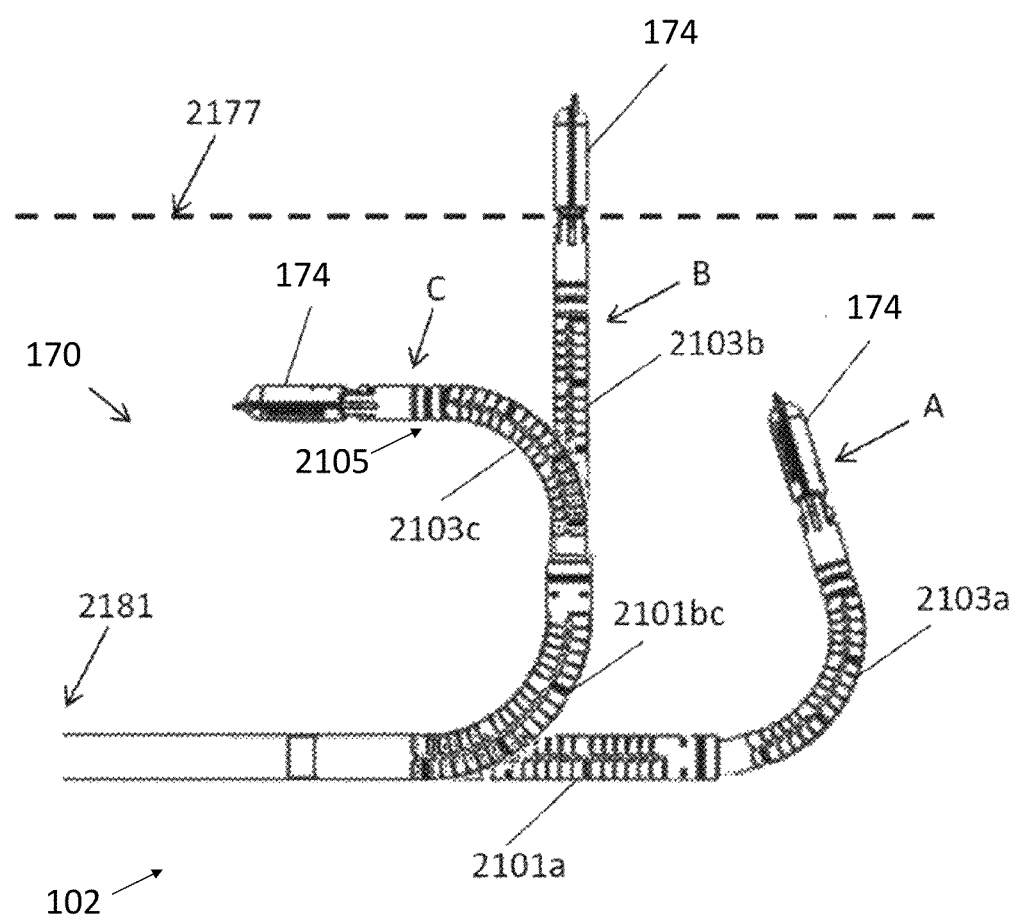
FIGS. 3A, 3B and 3C show the distal portion of a mechanical surgical arm in a variety of flexed and retroflexed positions, according to embodiments of the present invention.

The terms 'elbow joint', 'wrist joint' and 'shoulder joint' where used herein refer to particular joints of a mechanical arm, according to a specific implementation in which the arm comprises three actuatable joints. In such a case, the joint nearest a distal-end effector is known as the 'wrist joint', the middle joint of the three is the 'elbow joint' and the most proximal joint is known as the 'shoulder joint'. In some embodiments, a wrist joint is limited to rotation only, i.e., is not configured to flex. The various joints are shown in FIG. 3A, which is discussed hereinbelow.

The meaning of the term 'joint' unless otherwise specified and as used in this disclosure and in the appended claims in the case of arm joints, i.e., joints of an arm, means any actuatable member capable of causing a flexion (e.g., planar bending) and/or a rotation. It should be noted that articulatable/avatar-like input arms (a type of input device) can also have joints, and they are referred to as 'joint members' of the input devices. Typically, arm segments are non-actuatable (with respect to flexing/rotating) members of an arm which can be joined serially by actuatable arm joints, where the term 'joined serially' means only that a joint is interposed between two consecutive segment members. A joint can be actuated, e.g., mechanically and/or electronically, to cause a flexion of one arm segment (and every portion of the arm disposed distally therefrom) relative to a base arm segment (2181 In FIG. 3A) or another (adjacent) arm segment, and/or to cause a rotation of one arm segment (and every portion of the arm disposed distally therefrom) relative to the base arm segment or another arm segment. In some embodiments, a joint includes multiple components, and in some examples can include both a flexion-facilitating component (or subassembly and a rotation-facilitating component (or subassembly). For the sake of readability, a combination of such components is referred to herein, in combination, as a joint or an arm joint.

In embodiments, arm movements may be limited according to types of articulations (e.g., rotations vs. flexions), speed of movement, which portions of the surgical arm can move, etc. Movement of the surgical arm during the first operating mode can be restricted to movement of a given single arm joint—an elbow joint only—(including, for example, flexion and/or rotation of the elbow joint) and to linear movement of the surgical arm as a single unit (including, for example, linearly advancing and retracting the arm). It can be desirable to limit arm movements during the first operating mode to facilitate introducing the surgical arms with minimized volume through a narrow path and to the target surgical site.

It can also be desirable to limit arm movements during the first operating mode to facilitate retroflexing of the arm in a minimum volume so as to avoid collision and potential tissue damage within the human body. FIG. 3A is a simplified schematic side view of a surgical mechanical arm 102 in different configurations, explained here for illustrative purposes. The dashed line 2177 represents an obstacle, for example patient tissue. Movements of the arm 102 when retroflecting are preferably controlled to prevent contact or collision of the arm 102 (and especially end effector 174) with the obstacle 2177. Three scenarios, respectively labeled A, B and C are illustrated in FIG. 3. Arm 102 comprises proximal segment 2181 and distal bendable portion 170. Bendable portion 2179 comprises shoulder joint 2101 and elbow joint 2103, which are labeled variously as 2101a, 2101bc, 2103a, 2103b and 2103c so as to indicate to which one or more of the scenarios (A, B or C) the instance of the joint is relevant. For example, joint 2103a is the elbow joint position in scenario A. Thus, scenario A involves the bending of only elbow joint 2103a (shoulder joint 2101a remains unactuated and unbent), and specifically one can see that the bending of only elbow joint 2101a does not cause a collision between end effector 174 and the obstacle 2177. On the other hand, in Scenario B, in which only the shoulder joint 2101b is bent, there is a collision between end effector 174 with the obstacle 2177. The difference between the collision/no-collision results of Scenarios A and B is because the portion of the arm 102 distal from the elbow joint 2103 is shorter than the portion of the arm distal from the shoulder joint 2101. The wrist joint 2105 of arm 102 in FIG. 3A is not involved in any of the three scenarios, as being designed or configured in the non-limiting example of FIG. 3A to rotate but not flex. In scenario C, which is a continuation of scenario A, it can be seen that flexing shoulder joint 2101c after the flexion of elbow joint 2103a (now 2103c) can facilitate the continued avoidance of collision between end effector 174 and obstacle 2177.

Figure 3B:
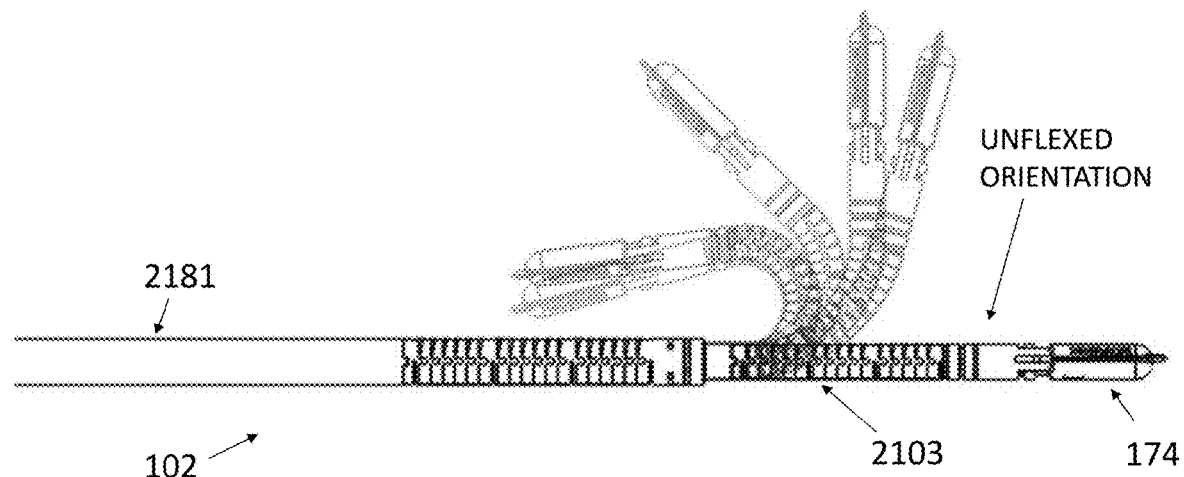

FIG. 3B illustrates examples of elbow joint 2103 flexion from an unflexed orientation to various post-flexion orientations ranging from less than 90° to more than 180° relative to proximal arm base segment 2181.

Figure 3C:
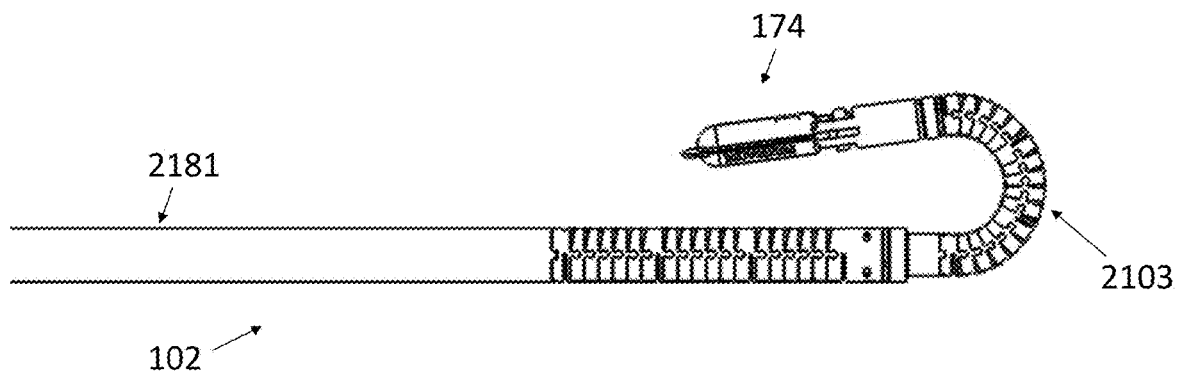

In embodiments, the flexion range of movement for an elbow joint is >90°, >120°, >140°, >160°, >180°, >190°, >200° or about 210°±10°. In some embodiments, an end-effector 174 is capable of being positioned at >90°, >120°, >140°, >160°, >180°, >190°, >200° or about 210°±10° relative to the base 2181 of the arm 102. In some embodiments, an end-effector 174 is able to be parallel to the base 2181 of the arm 102 or alternatively reach the base 2181 of the arm 102 when fully flexed. In addition, the Elbow Rotation joint range of motion shall be at least 200°, at least 250°, at least 300°, at least 310°, at least 320°, at least 330°, at least 350° or about 360°. FIG. 3C shows an arm 102 with flexion of elbow joint 2103 of more than 180° rotated from the unflexed orientation indicated in FIG. 3B, so as to bring the arm 102 to a retroflex configuration or, equivalently, retroflex position, and so as to deliver end effector 174 to a retroflex operation position.

In some embodiments, the retroflexion of a surgical arm can be done automatically, i.e., by arranging the arm to respond to a single or limited number of electronic control-outputs by flexing and/or rotating a single arm joint until a pre-programmed retroflex position of the arm and/or of an end effector at the distal end of the arm is achieved.

Figure 4:
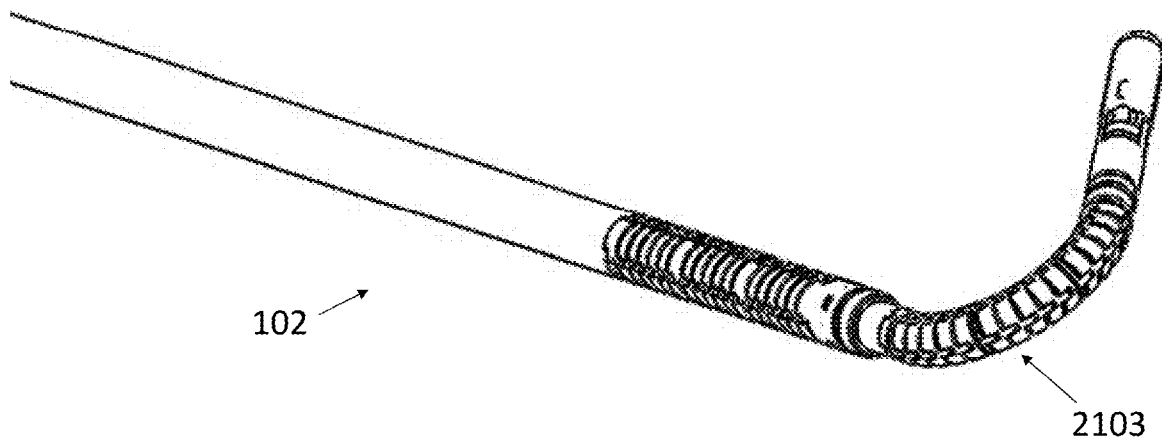
FIGS. 4 and 5 show the distal portion of a mechanical surgical arm with a variety of arm curve-shapes, according to embodiments of the present invention.

FIG. 4 shows, in front perspective, an arm 102 with elbow joint 2103 flexed similarly to elbow joint 2103a in scenario A of FIG. 3B, and subsequently rotated—i.e., elbow joint 2103 in FIG. 4 is both flexed and rotated. The rotation of any arm joint can be independent of the flexion of the same arm joint. In some embodiments, the flexion and rotation can be simultaneous, and in other embodiments, a restriction of non-simultaneity can be enforced, for example by hardware design or by a software component of control circuitry governing the actuation of the joint.

Figure 5:
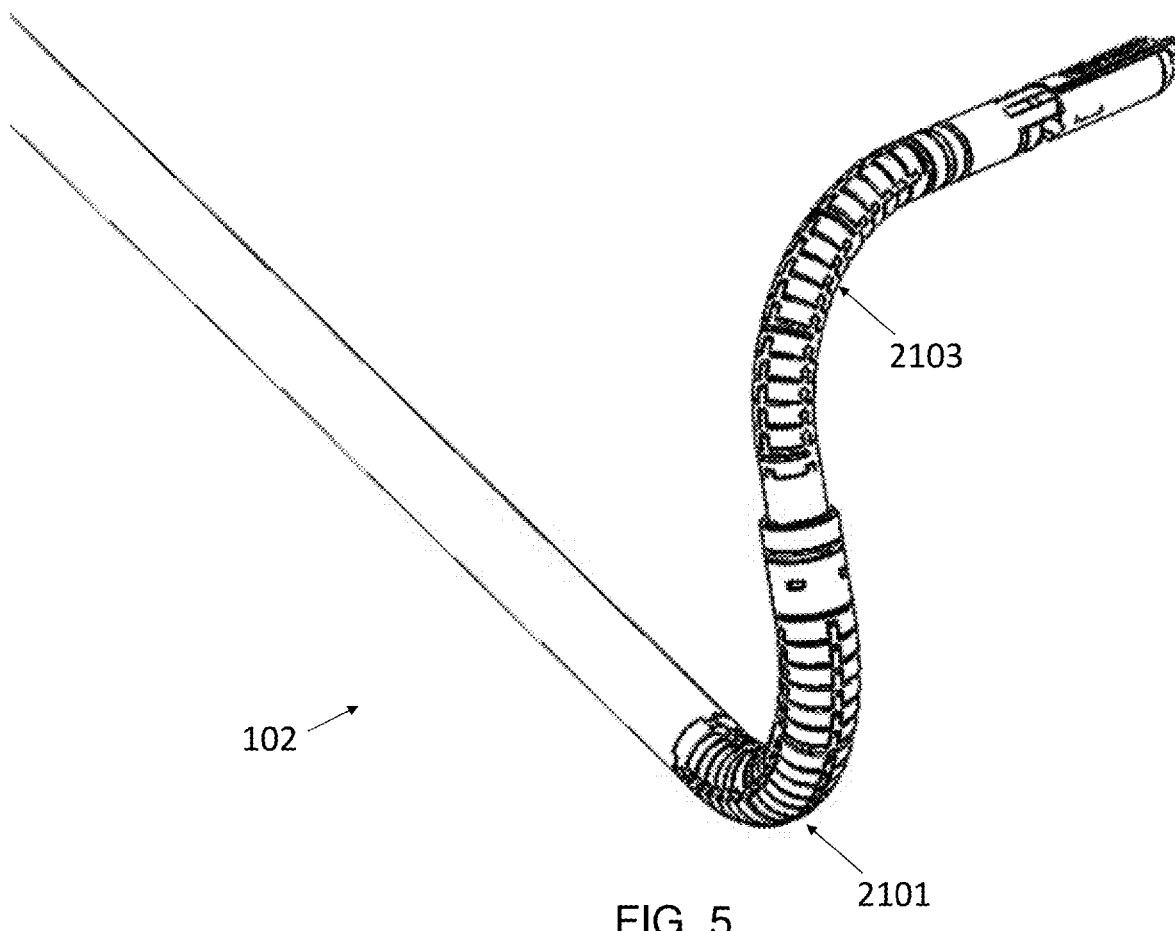

FIG. 5 shows, in front perspective, an arm 102 with elbow joint 2103 flexed and rotated similar to that of FIG. 4, and with shoulder joint 2101 flexed so as to form, together with elbow joint 2101, a complex "S" shape. In some embodiments, such as those typified by scenario C of FIG. 3B, the shoulder joint 2101 is preferably actuated to flex and rotate only after the flexing of the elbow joint 2103 has 'cleared' the obstacle 2177.

Figure 6:
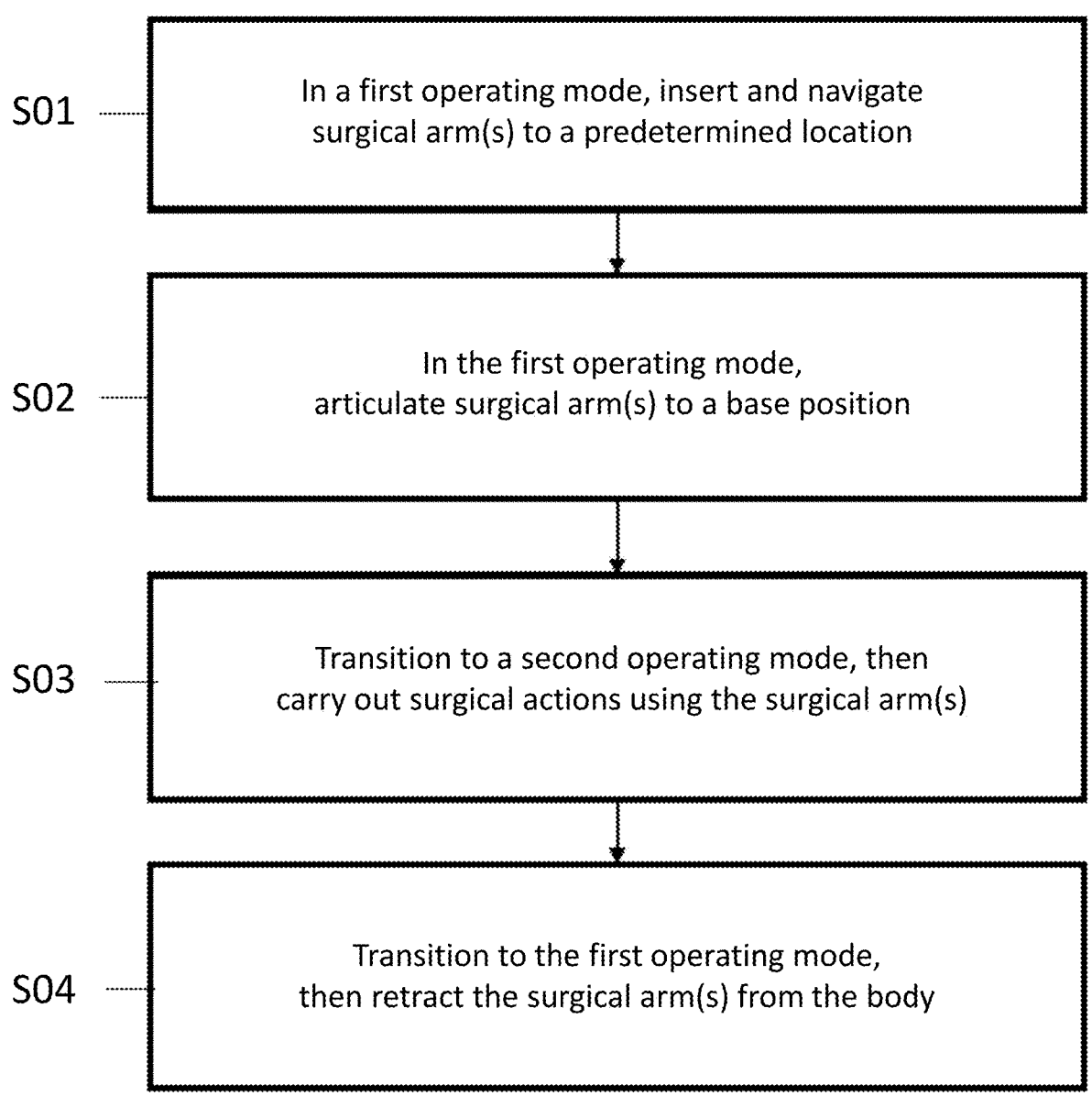
FIG. 6 shows a flowchart of a method for operating surgical mechanical arms using two operating modes, according to embodiments of the present invention.

Referring now to FIG. 6, a flowchart of a general method is shown for controlling surgical mechanical arms using different operating modes, according to some embodiments.

A process for example as described herein may be implemented for various types of operations such as gynecologic, laparoscopic, otorhinolaryngology (ear, nose and throat) surgeries, carried out, at least in part, using one or more surgical mechanical arms inserted into the body of a patient.

As discussed hereinabove, the surgical mechanical arms can be operated according to a plurality of operating modes. Optionally, the operating modes are selected in accordance with a surgical step to be performed and/or in accordance with a current stage of the surgery.

Different operating modes can be characterized by different ways of translating user inputs (movements of input devices or control elements of input devices), i.e., by manipulation of user-input devices, into respective movements of the surgical mechanical arms. Additionally or alternatively, different operating modes can be characterized by different restrictions on surgical arm articulation, for example, limiting articulation (e.g. flexion) of one or more surgical arm joints; limiting a range of movement; or limiting arm articulation to selected degrees of freedom. Additionally or alternatively, different operating modes can be characterized by different types of feedback to the user, for example, feedback sensed by a user controlling the surgical arms via one or more input devices.

In some embodiments, selecting and/or switching between operating modes is controlled by a user, e.g. a surgeon. Optionally, selection of operating modes can be carried out via a user interface of the system, for example via a touch screen and/or via buttons or other input devices disposed on or in proximity to another input device, or a control console or display screen. Additionally or alternatively, selecting operating modes can be automatic, for example, carried out by suitable control circuitry, such as by a system controller or processor. In some embodiments, selecting and/or switching an operating mode is triggered by and contingent upon: one or more of, and not exhaustively: identifying the current 'anatomical' position of the surgical arm or of the end effector of the arm, for example, by using electromechanical instruments such as encoders or other sensors (NOT SHOWN) associated with the actuators and/or motors (e.g. of 104 or 108) of the arms, or by accessing and analyzing images of arm 102 obtained by a camera—through image processing or visually, upon identifying a current position of the input device, upon performing a certain articulation of the surgical arms, upon receiving an indication of one or more position sensors of the surgical arms, upon a timed indication, for example by setting a time point by which an operating mode is changed.

The flowchart in FIG. 6 describes a method of operating surgical mechanical arms using two operating modes, according to some embodiments.

The method includes:

Step S01: inserting and navigating surgical arm(s) to a predetermined location in a first operating mode.

In a first operating mode, the surgical arms are introduced into the body and navigated to a selected anatomical location and/or to a selected arm position. The surgical arms may be introduced to the body via a natural body orifice (e.g., the vagina, anus, trachea, esophagus, ear canal) and/or via an incision.

In some embodiments, in the first operating mode, arm articulation is limited. For example, one or more arm joints can be restricted or precluded from articulating (flexing and rotating). In an example, the arm comprises 3 joints: a shoulder joint, an elbow joint and a wrist joint that rotates but doesn't flex, and one or two of the joints are prevented from articulating. In a specific example, only movement of the elbow joint is allowed, e.g. flexion, extension and/or rotation of the elbow joint, while the shoulder and wrist joint are restricted from moving.

It can also be that while in the first operating mode, the arm as a whole is allowed to move linearly (including only linearly), such as to be advanced or retracted in a one-dimensional movement.

In some embodiments, restriction of arm movement is achieved mechanically, for example by one or more locks (e.g. solenoid locks) affecting actuation of the arm joints. Additionally or alternatively, restriction of arm movement can be achieved by suitable circuitry, for example, by implementing software control functions that limit the extent of movement and/or the type of movement.

In some embodiments, limiting an extent of arm movement and/or restricting certain types of movement is performed in accordance with a current arm position, as indicated, for example, by one or more position sensors of the arm. In some embodiments, limiting an extent of arm movement and/or restricting certain types of movement is performed in accordance with a current anatomical location of the arms, for example as visualized by optical means (e.g. a camera introduced into the body, optionally along with the surgical arms).

Step S02: articulate surgical arm(s) to a base position in the first operating mode Still in the first operating mode, the surgical arm(s) is(are) articulated to a base position. In some embodiments, the base position comprises a retroflected position of the arms, for example, when the arms are flexed by at least 120 degrees, at least 150 degrees, at least 180 degrees or intermediate, larger or smaller angles. In some embodiments, the base position is one in which the arms are positioned to allow a user to perform surgical acts from a selected orientation (e.g. corresponding to an abdominal orientation) which the user may be more comfortable or familiar with.

In some embodiments, control of surgical arm movement in the first operating mode comprises robotic control. Optionally, manipulation of an input device by a user in the first operating mode involves only limited types of user movement, for example, limited movement of an input device along a defined axis and/or pressing of buttons. In an example, moving the input device along a first defined axis actuates rotation of selected arm joint, e.g. elbow; moving the input device along a second defined axis actuates flexion of a selected arm joint, e.g. elbow; pushing one or more buttons actuates linear advancement or retraction of the surgical arm.

In some embodiments, manipulation of an input device by a user in the first operating mode is translated to the speed of movement of the surgical arm. For example, when the user moves an input device relative to the rest position of the input device, the extent to which the input device was moved relative to its rest position sets the relative speed of movement of the surgical arm.

Step S03 Transition to a second operating mode, then carrying out surgical actions using the surgical arm(s)

In a second operating mode, the user carries out surgical acts via the surgical arms, for example grasping tissue, dissecting tissue, moving tissue, suturing tissue. In some embodiments, the second operating mode is initiated at the end of step S02, once the arms have been moved into a selected base position, for example, a retroflected position.

In some embodiments, the user switches an input device when transferring from the first operating mode to the second operating mode. Alternately, the user uses the same input device for both the first or navigation operating mode and the second or surgical operating mode.

In some embodiments, at the second operating mode, surgical arm movement is not as restricted as in the first operating mode. In an example, all arm joints (shoulder, elbow, wrist) are allowed to articulate, e.g. bend and/or rotate. In some embodiments, the extent and/or speed of arm movement during the second operating mode is limited based on safety considerations, for example, not to damage surrounding tissue, not to perform a movement at a speed that is too high and may risk damage.

In some embodiments, control of the surgical arms at the second operating mode involves tele-operated control. Optionally, displacement of an input device by the user is mimicked by a respective displacement of the surgical arm. Optionally, the speed of displacement of an input device by the user is reflected in the respective speed of surgical arm movement.

Step S04 Transition back to the first operating mode, then retract the surgical arm(s) from the body In accordance with some embodiments, optionally when the surgical acts have been accomplished, the arms are retracted outwardly from the patient body. In some embodiments, retraction is performed in the first operating mode. Optionally, before and/or during retraction, the arms are straightened.

Retracting in the first operating mode may be advantageous as it limits the extent and/or type of arm movement, thereby potentially reducing damage to tissues surrounding an anatomical passage (e.g. the vagina) through which the arms are retracted.

Referring now to FIG. 7, a control console 118 can comprise a display screen 407, with input devices 405 positioned in proximity thereto—on opposite sides of screen 407 in the non-limiting example of FIG. 7.

Each of the input devices 405 (in the form of 'thumbsticks') comprises a nipple-type controller 409 suitable for manipulation by a user's thumb. In embodiments, the extent of movement of the nipple 409 relative to a central rest position can be translated to a velocity of a chosen surgical arm movement, as discussed hereinabove. In one example, the further the nipple 409 is pushed away from its central rest position, the higher the resulting speed of the movement of the surgical arm. In another example, the more force is applied to the nipple 409, the higher the resulting speed of the movement of the surgical arm.

In some embodiments, when controlling the surgical arms via the thumbsticks 405, one or more of the surgical arm joints (e.g. a shoulder joint, a wrist joint) are restricted from movement, and only flexion and/or rotation of the elbow joint are enabled. In some embodiments, linear movement of the surgical arm (as a single body) is also enabled, for example to advance or retract the arm. In some embodiments, movement of the nipple 409 actuates flexion and/or rotation of the elbow joint. In some embodiments, linear movement of the arm 102 is actuated by separate actuators, for example using another pair of input devices such as input devices 406, 408 which are implemented as push buttons disposed, in the illustrated example of FIG. 7, along the body of the input devices (thumbstick assembly) 405 themselves. In other examples the push buttons 406, 408 can be provided independently, or on (or in closer proximity to) the display screen 407. In an example, button 406 advances the surgical arm distally (e.g. in an abdominal direction) and button 408 retracts the surgical arm proximally. In embodiments, input devices 406, 408 may be used while in a first mode in which flexing and rotating arm joints that are not the elbow joint is precluded, as the linear motion does not require any flexing or rotating.

In some embodiments, during use of the thumbsticks 405, other input devices such as avatar-input arms 411 provided for use in the second mode without any first-mode restrictions, are locked at a rest position, for example by solenoid locks. In some embodiments, the rest position of the input arms 411 is selected as the retroflected position of the surgical arm 102, so that once the surgical arms 102 have been retroflected (e.g. using the thumbsticks), a user may pick up the avatar input arms 411 and continue the procedure directly. In some embodiments, when the avatar-like input arms 411 are enabled while in the second mode, operation of the thumbsticks is disabled.

In some embodiments, during insertion of the surgical arms 102 into the body of a patient 106, the surgical arms are straight, i.e., unflexed. In some cases insertion is via a cannula. At the same time, the avatar input arms are at a rest position, which can be a locked position and which can be a retroflexed position. Optionally, following retroflection of the surgical arms using the thumbsticks 405, the surgeon may release the thumbsticks 405 and moves her hands to the avatar input arms 411. Once the avatar input arms 411 are grasped and optionally lifted by the surgeon, control over the surgical arms 102 can be automatically transferred or transitioned from the first user-input device 405 to the second 411, and the surgeon may continue the procedure using the avatar input arms 411.

In some embodiments, when one or more avatar input arm joints are locked by solenoid locks, lifting of the avatar input arm by the surgeon automatically releases the solenoid locks. Additionally or alternatively, manual locks of the avatar input arm joints are released, for example via a sensor that detects an avatar input arm position.

In some embodiments, the system (e.g. a system processor) is configured to recognize one or more positions of the input devices, for example a current position of the thumbsticks and/or a current position of the avatar input arms, and optionally to present the position on the user interface screen. In some embodiments, identifying a position is assisted by the use of position sensors.

FIG. 8 shows an image of an example of a thumb-operated input device 501 comprising a gripping handle 503 and, optionally, a textured surface to facilitate gripping, such as a surface comprising ridges 505. One or more control buttons 507 can be disposed along the gripping handle 503. For example, the thumbstick input device 501 of FIG. 8 comprises two control buttons 507—one for actuating linear advancement of the surgical arm distally, and one for actuating linear retraction of the arm proximally.

In some embodiments, thumbstick 501 comprises a nipple 509, extending for example from a proximal end of the gripping handle 503. In some embodiments, nipple 509 is shaped and/or sized for a user's thumb. In some embodiments, nipple 509 comprises a rounded profile. In some embodiments, a proximal surface of the nipple 509 is formed with circumferential protrusions 511. The circumferential protrusions may assist in maintaining the thumb placed on the nipple 509, potentially preventing or reducing sliding of the thumb away from the nipple 509.

In some embodiments, the nipple 509 moves in a spring-like manner. Optionally, after pushing the nipple 509 away from its initial rest position (e.g a central position, in which the nipple 509 is centrally aligned with long axis 513 of the thumbstick), the nipple springs back to its central position.

FIG. 9 is a schematic diagram illustrating an example of control of the thumb-operated input 501, according to some embodiments. In some embodiments, moving ('displacing') the nipple 509 with respect to first axis actuates a first type of surgical arm movement, for example a flexion; and displacing the nipple 509 with respect to a second axis actuates a second type of surgical arm movement, for example rotation.

In some embodiments, the thumbsticks 501 are used during the first operation mode, when at least some of the joints are restricted, for example, the shoulder and wrist joints 2101, 2105. Optionally, displacing the nipple 509 along the Y-axis generates flexion of an elbow joint 2103 of the surgical arm 102; and displacing the nipple 509 along the axis generates rotation of the elbow joint. In some embodiments, actuation of simultaneous bending and rotation can be achieved by pushing the nipple relative to both axes, for example, diagonally relative to the center.

Figure 10:
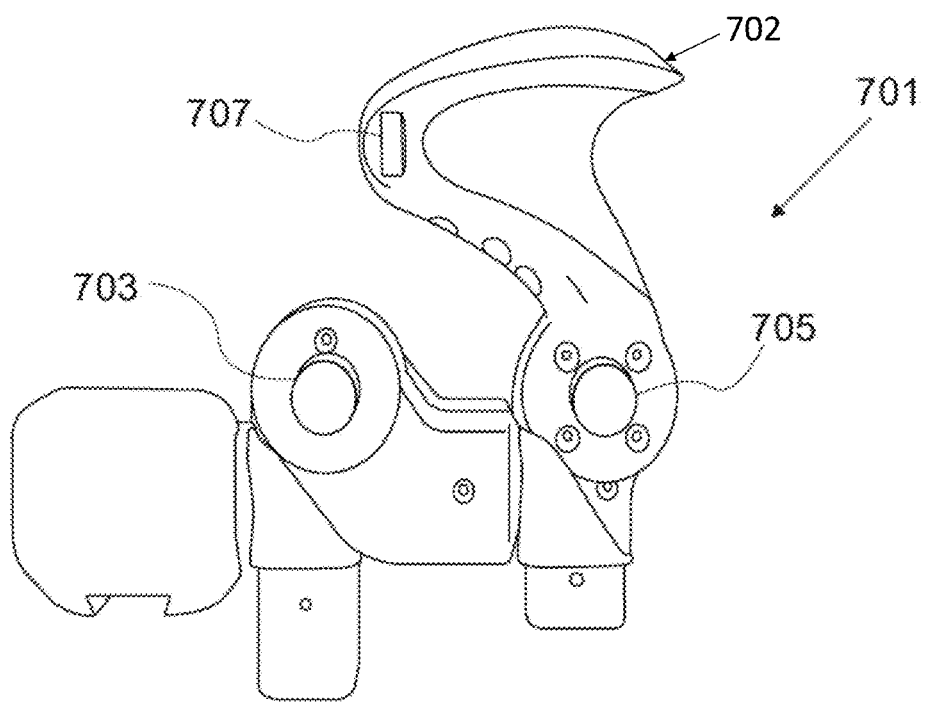
FIG. 10 is a schematic illustration of an articulated user-input device according to embodiments of the present invention.
Figure 11:
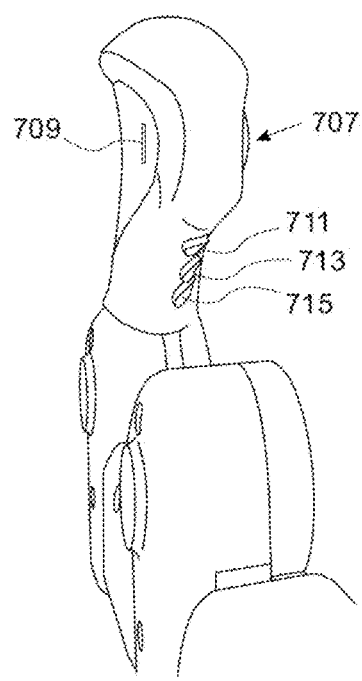
FIG. 11 is a schematic view of a handle member of the user-input device of FIG. 10 according to embodiments of the present invention.

Referring now to FIGS. 10 and 11, side and front view images are shown of an exemplary avatar-like input arm 701 comprising multiple joints for actuating respective movement of surgical arm joints: as illustrated the joints include a shoulder joint 703, an elbow joint 705 and a wrist rotation knob 707 for controlling a wrist joint 2105 of a surgical arm 102.

In some embodiments, the avatar input arm can comprise additional input devices, such as button or lever 709, which can control operation of a surgical tool (as end effector 174) of the surgical arm 102.

Other input devices disposed on the exemplary input arm 701 of FIGS. 10-11 include a pause-resume button 711 and buttons 713, 715 respectively for actuating linear advancement and retraction of the arm 102. A user may use the buttons 713, 715 on the avatar input arm and/or the buttons 406, 408 disposed on the thumbstick 405 to actuate linear advancement and/or retraction. Additionally or alternatively, linear movement of the arm may be actuated via a screen interface of the control console (e.g. via a touch screen interface).

In some embodiments, a set of two avatar input arms are provided, for controlling left and right arms respectively. For example, a first avatar input arm 701 can control a first motor unit 108 associated with a first surgical arm 102 (e.g. a "right" arm) and a second avatar input arm 701 can control a second motor unit 108 associated with a second surgical arm 102 (e.g. a "left" arm). In some embodiments, any or all of input arms 120, 411 and 701 can be the same.

We now refer to FIGS. 12A and 12B. In embodiments, alignment of an input device such as the avatar input arm with the current position of the surgical mechanical arm is performed. In an example, alignment is performed when the user switches between different input devices, for example when switching from thumb operated input to the avatar input arm. In another example, alignment of an input device with the surgical arm position is performed upon initialization of the system, for example at the beginning or prior to surgery. In another example, an alignment of the input device with the current position of the surgical mechanical arm is performed when resuming control following a pause. Optionally, in the paused mode, movement of the input device does not actuate relative movement of the surgical mechanical arm, and upon resuming control, it may be required to adjust a position of the input arm so that it matches the current position of the surgical mechanical arm, to continue operation in a smooth, non-interrupted manner.

In some embodiments, resumed control is gained in an automatic or semi-automatic manner. For example, a user performs a selected articulation of the input device (e.g. straightens an elbow joint of the avatar input arm) and control of the surgical arm is resumed.

In FIGS. 12A and 12B, the relative position of an input device (i.e., input arm) is represented using a cross shaped diagram 801. In some embodiments, there are two sets of crosses, one for the shoulder joint and one for the elbow joint. In some embodiments, the cross represents a specific single joint (e.g. a shoulder joint, an elbow joint) of the surgical mechanical arm. In some embodiments, each line of the slot represents a different type of articulation, for example, the horizontal line 803 represents rotation of the joint; the vertical 805 line represents flexion of the joint. During use, a user manipulates the input device according to the joint position indicated at the cross by the two colored dots 807. As the position of the input device (in response to manipulation by the user) becomes closer to that of the surgical mechanical arm, the colored dots move closer to the center of the cross (see FIG. 12B). Optionally, once sufficient alignment between the input device position and the surgical arm position is obtained, the dots change color, for example, from red to green as indicated in FIGS. 12A-B.

In embodiments, the control apparatus of FIGS. 12A and 12B can be used in an alignment calibration as part of a transitioning from a first mode using a first input device to a second mode using the avatar-like input arm. In these embodiments, the first input device can be used to adjust the position of the surgical arm so as to align with a fixed position of the input arm.

FIG. 13 is an example of a screen displayed to the user during alignment, according to some embodiments. In the shown example, a first input device (such as corresponding with the right avatar arm) is shown to be properly aligned with the first surgical arm, as indicated for example by the checkmarks 809 at the position of both the elbow and shoulder joints, and/or by the locked lock 811. A second input device (such as corresponding with the left arm) is shown at a position in which it is not yet aligned with the surgical arm. The joint position is represented by the two cross shaped diagrams, for example as described hereinabove, and the lock is unlocked.

In some embodiments, during alignment, certain articulations and/or functions are disabled, for example, the speed of the surgical arm is limited; electrosurgery functions are disabled; and/or other functions.

FIGS. 14A-E show a set of images showing exemplary control of surgical mechanical arms using a plurality of different input devices, according to some embodiments. Two arms are shown in the non-limiting example of FIGS. 14A-E, and in other examples there can be a single arm or more than 2 arms.

Figure 14A:
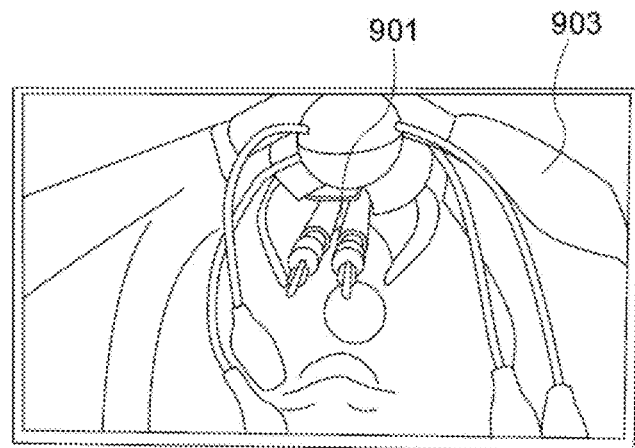
FIGS. 14A-E show time-consecutive images showing exemplary control of surgical mechanical arms using a plurality of different input devices, according to embodiments of the present invention.
Figure 14A:
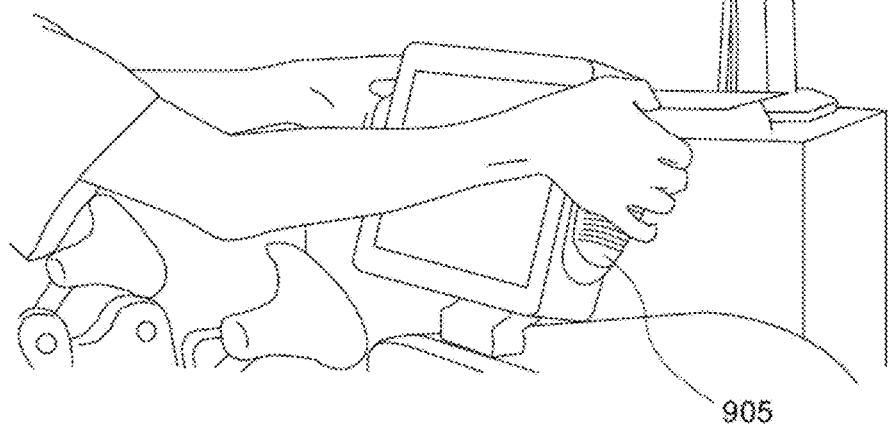

FIG. 14A shows control of two surgical mechanical arms 901 during introducing of the arms into a model 903 simulating access to the body via the vagina, according to some embodiments. In this example, control of the surgical arms 901 during advancing of the arms into the body (e.g through the vaginal canal) is via thumb-operated input, including a set of thumbsticks 905 for example as described hereinabove.

Figure 14B:
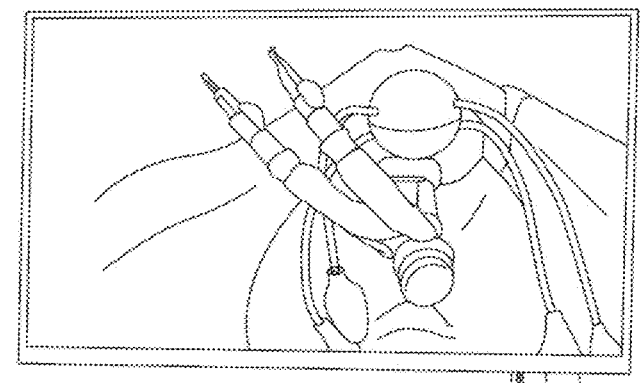
Figure 14B:
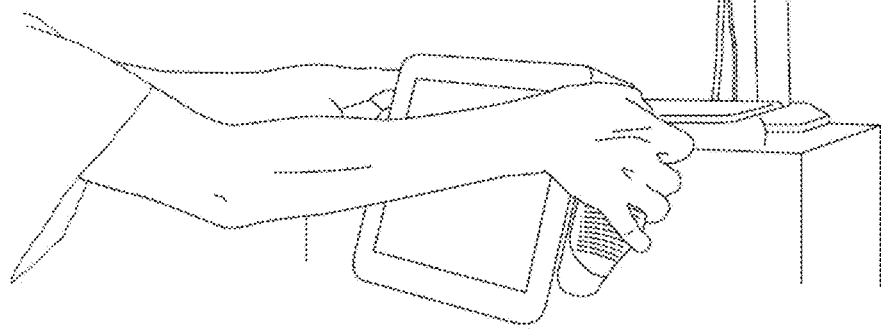

FIG. 14B shows manipulation of the surgical arms, via the thumbsticks 905, into a retroflected position. In the shown example, the arms are flexed (e.g. by 120, 150, 180, 210 degrees or intermediate, larger or smaller angles) to obtain the retroflected position.

Figure 14C:
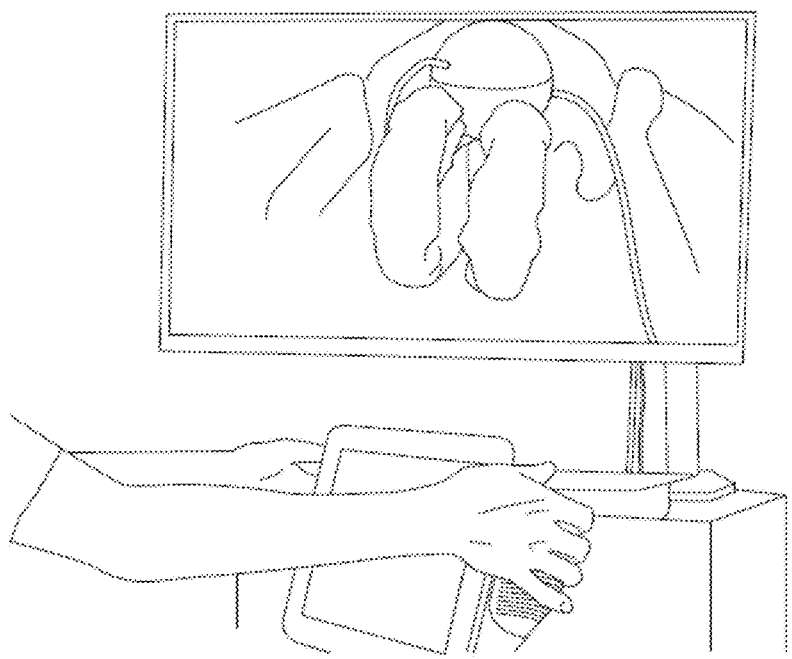

FIG. 14C shows the surgical arms in a retroflex position. Following retroflection, a user may, in some examples, switch the input device used, for example by releasing the thumbsticks and picks up avatar input arms. At this point, alignment of the avatar input arms with current a position of the surgical arms can be performed, for example as described in FIGS. 12A-B and 13.

Figure 14D:
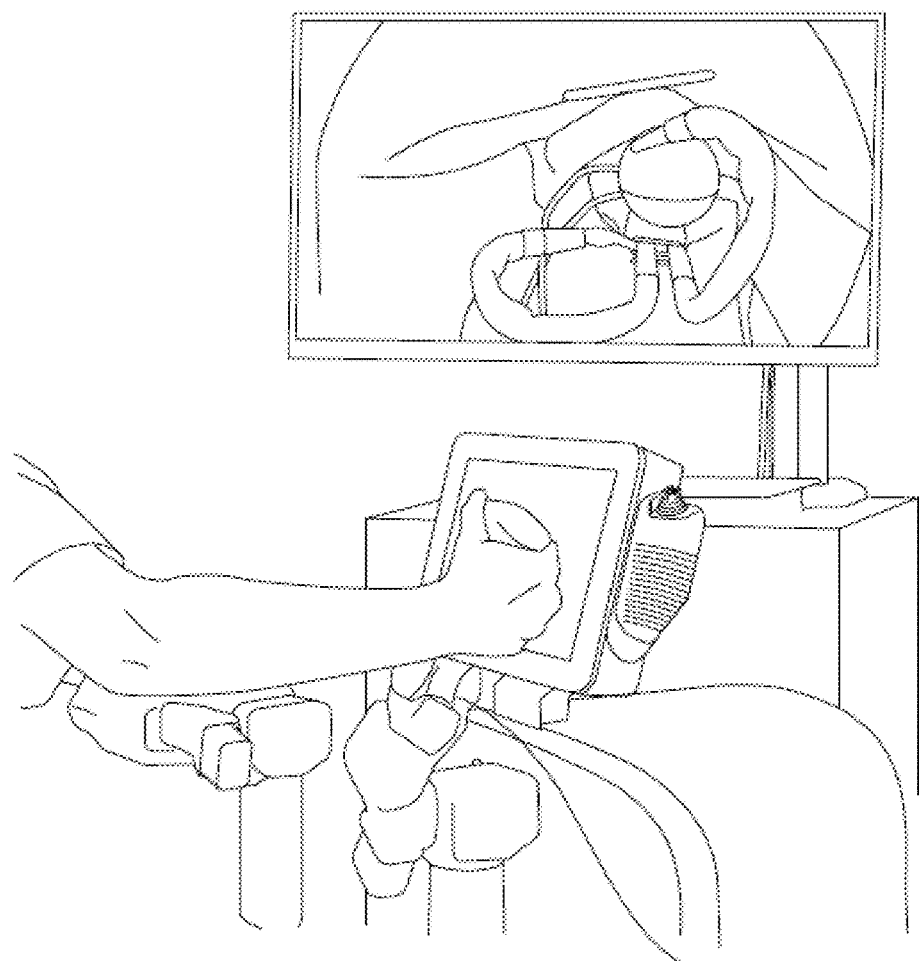
Figure 14E:
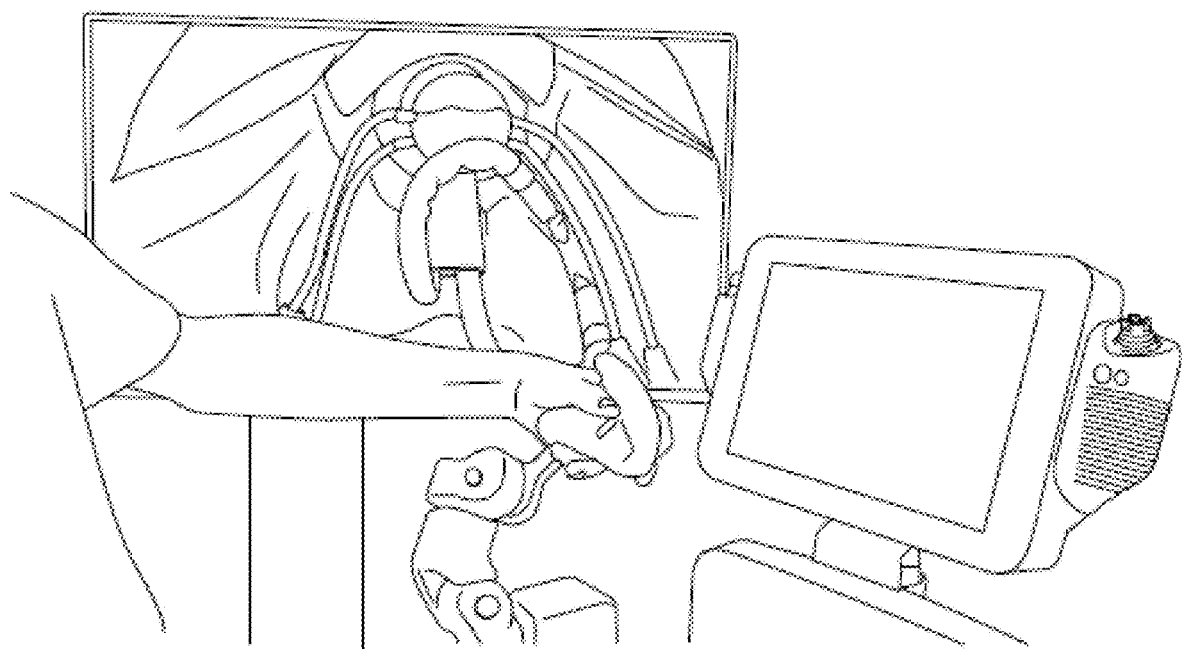

FIGS. 14D and 14E show maneuvering of the surgical arms using a set of avatar input arms 907, according to some embodiments. It can be seen that the respective positions of the surgical arms correspond to the positions of the input arms.

Figure 15:
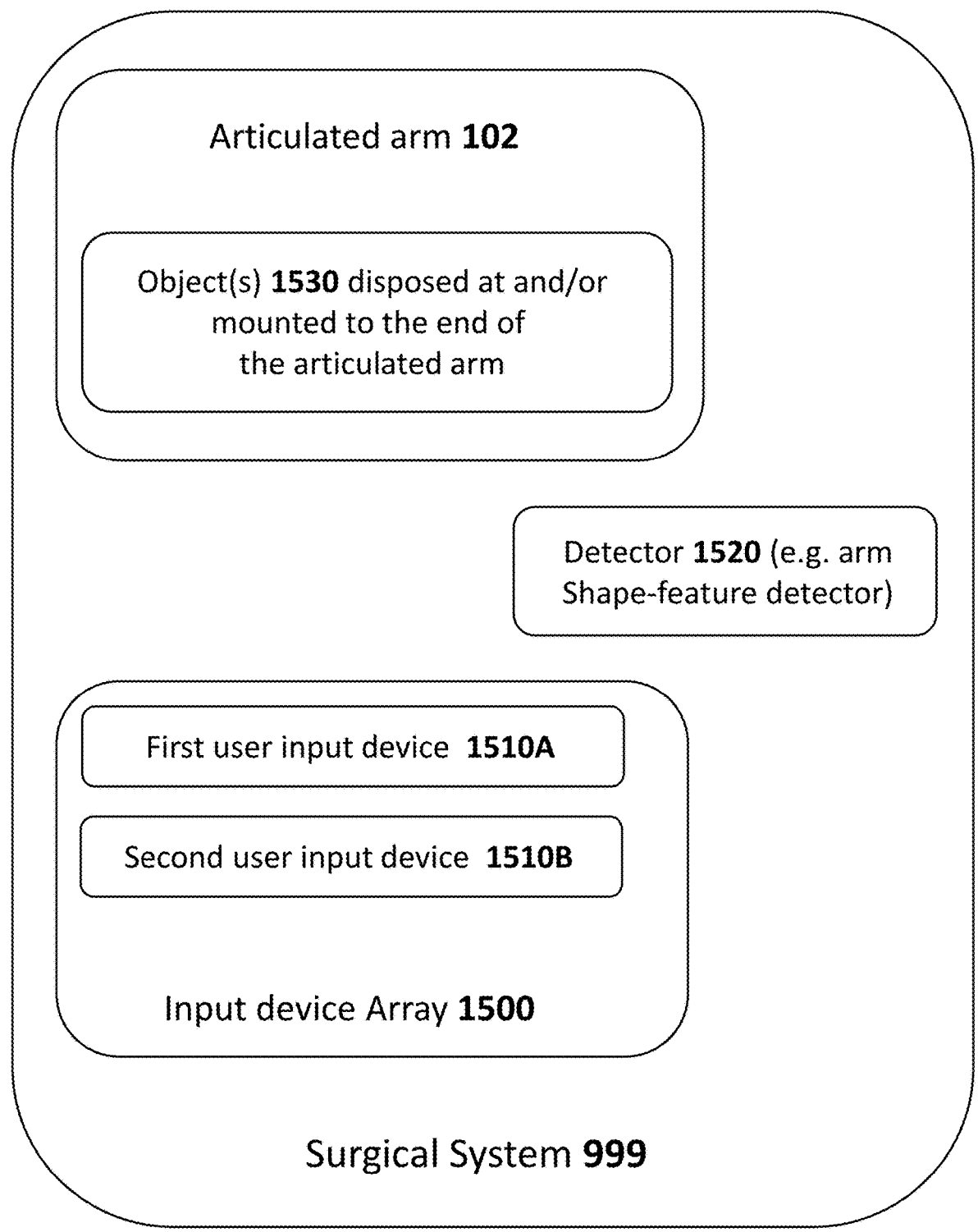
FIG. 15 shows a block diagram of a surgical system according to embodiments of the present invention.

The block diagram of FIG. 15 shows articulated arm 102, input-device array 1500, and detector 1520. The skilled artisan will appreciate that not every element appearing in FIG. 15 is required in every embodiment. Although input-device array 1500 as illustrated in FIG. 15 shows two user input devices 1510A (e.g. thumbstick 501), 1510B (e.g. joystick 701), the skilled artisan will appreciate that in different embodiments fewer or more user-input devices may be provided. In an example, the joystick 701 can be both the first user-input device 1510A and the second user-input device 1510B; in other words, the first user-input device 1510A and the second user-input device 1510B can be the same single user-input device. In implementations in which the first user-input device 1510A and the second user-input device 1510B are the same single user-input device, then it is typically the more versatile or flexible device such as the joystick 701. The term user-input device relates to a device for converting input received by a user into electronic output and/or signals. Examples of user-input devices include but are not limited to joysticks, touch screens, thumbsticks, mouse, keyboards, gesture detection devices (e.g. including a camera [not shown]). Unless specified otherwise, the term "array" relates to one or more of an item.

As shown in the example of FIG. 15, articulated arm 102 has one or more objects 1530 mounted at a distal end thereof. The object(s) 1530 can be provided with the arm 102 or can be added or exchanged separately. Examples of such objects 1530 include but are not limited to end effectors, e.g., surgical end effectors. Relevant surgical tools can include, and not exhaustively: an endoscope for diagnostic/ surgical feedback, surgical end effector tools such as a needle driver (e.g., large needle driver, curved needle driver), mono and bipolar instruments (e.g., monopolar scissors, bipolar forceps), clip appliers (e.g., large and medium clip appliers), vessel sealers, graspers or dissectors (e.g., Maryland dissectors, Tenacululm forceps, micro forceps, long tip forceps, grasping retractors, Fundus graspers, Crocodile graspers, Cadiere forceps,), scissors (e.g., Potts Scissors, curved scissors), hooks (e.g., cautery hook), and spatulas (e.g., cautery spatula).

As discussed elsewhere, in some embodiments arm 102 and/or object(s) 1530 operate responsive to electronic control output of one or more of the control device(s). The terms 'control output' and 'control signal' are used synonymously. In different embodiments, the control output may be sent to arm 102 and/or to a controller thereof via wired and/or wireless communication.

Also illustrated in FIG. 15 is detector 1520. As discussed elsewhere, in some embodiments a mode transition from a first operating mode of surgical system 999 to a second operating mode of surgical system 999 is responsive to and/or contingent upon output of detector 1520. Surgical system 999 can be functionally equivalent to surgical system 100 shown in FIG. 1. In one non-limiting example, detector 1520 detects whether or not a portion (e.g. distal portion) of arm 102 is retroflexed and/or in a retroflex position. In one example, a camera may acquire an image of arm 102 and detector 1520 the camera and image-processing circuitry. In another example, encoders (not shown) or other electromechanical sensors (e.g. of 104 or 108) may be used for monitoring and detecting to track e.g. orientation of joint(s) of arm 102. Other examples may relate to magnetic or capacitive detector(s) or position detection based upon, e.g. (e.g. time-of-flight) triangulation using ultrasound and/or light.

'Monitoring' and 'detecting' as used in this disclosure and in the claims appended thereto are actions (and/or functions and/or potential actions and/or capabilities) which can be undertaken by one or more components of a surgical system, by one or more users, or any combination of system components and humans users. Descriptive language used herein with respect to automated or machine monitoring or detecting is meant as non-limiting, and in any such embodiment, user intervention can be a part of the design and/or a part of the operation. In some embodiments, user intervention is required for safety reasons. In a non-limiting example, one or more sensors relays information about a surgical arm or one of its components to a display screen to which a user is trained and/or positioned to monitor an arm curve-shape and detect, without or without automated or semi-automated visual aids, when an arm is in a desired position and orientation, e.g., is retroflected at a surgical worksite. In another non-limiting example, the monitoring and/or detecting is communicated to a user in a non-visual way, such as, and not exhaustively, by audible announcement, by haptic feedback, or by a locking of a control or input device. Obviously, any of these types of communications can be combined with visual information as well.

The skilled artisan will also appreciate that the additional elements may be provided in the surgical system 999, and that not every component of every element is illustrated in FIG. 15 is required in every embodiment.

Figure 16:
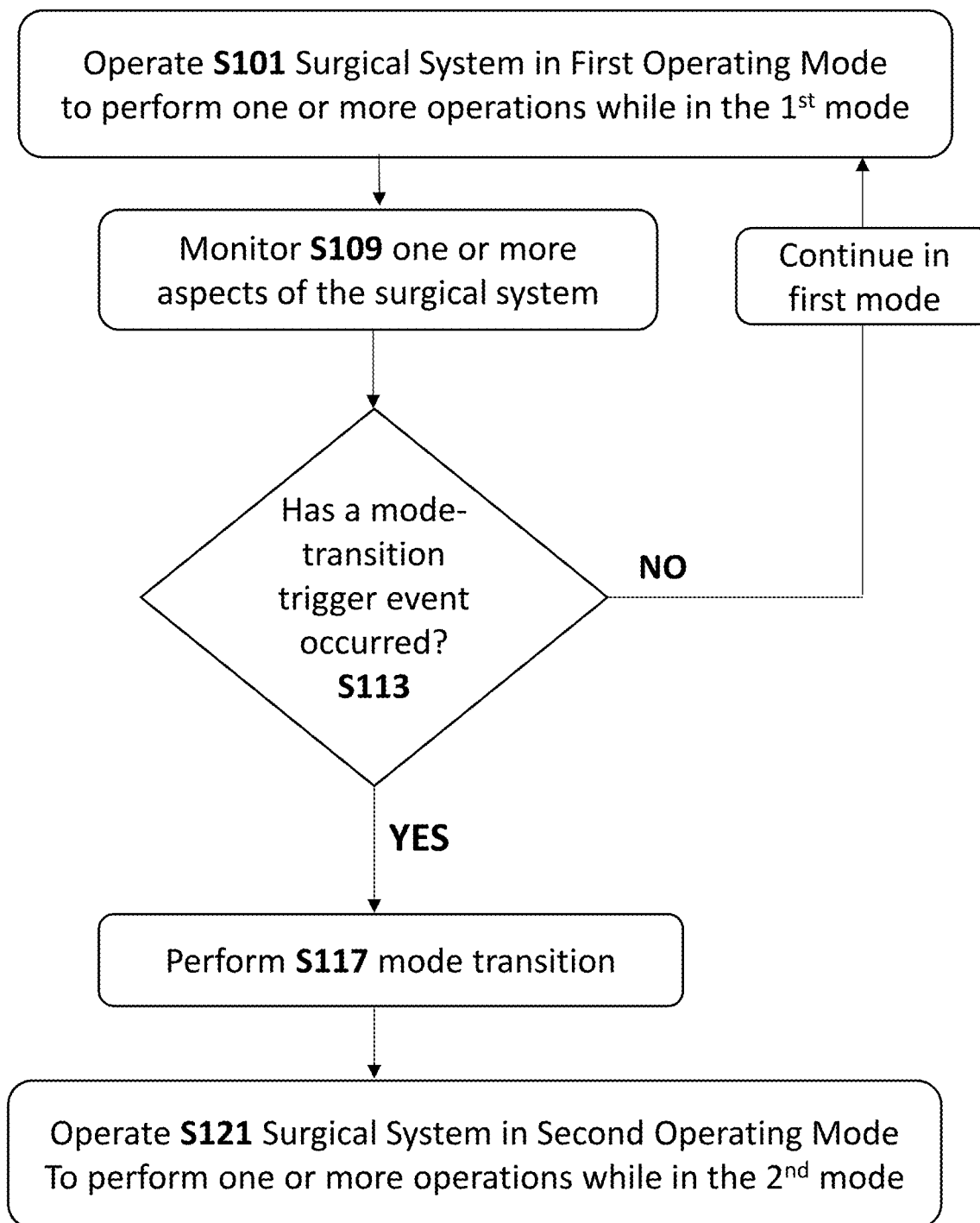
FIG. 16 shows a flowchart of a method for operating a surgical system in two different operating modes, according to embodiments of the present invention.

Reference is now made to FIG. 16. In step S101, surgical system 999 is operated in a first operating mode. In step S121, surgical system 999 is operated in a second operating mode. As discussed elsewhere, in different embodiments the first and/or second operating mode may relate to specific capabilities of and/or specific restrictions on one or more of the input devices. Alternatively or additionally, the first and/or second operating mode may relate to specific capabilities of and/or specific restrictions on one or more of elements of the arm 102 and/or objects 1530. Examples of such elements include joints and articulators. Alternatively or additionally, the first and/or second operating mode may relate to a relationship between operation of one or more input devices 1510 and arm 102 or one or more components thereof—e.g. whether or not a configuration of an input device 1510 or component thereof is translated into a speed or a position of arm 102 or component thereof.

While surgical system 999 is operated in the first mode in step S101, one or more operations are performed. In one example, when surgical system is operated in the first mode, a distal portion of arm 102 is retroflexed, possibly starting from an unflexed and/or straight position but not necessarily so. In another example, when the surgical system 999 is operated in the first mode, a distal portion of arm 102 is brought so a curve shape thereof, e.g. the curve shape in 3D or a planar projection thereof, matches a pre-determined curve shape, for example, one that is. useful for commencing surgical operations such as a retroflex shape or an "S" curve-shape.

Step S109 relates to monitoring and may be performed concurrent with step S101. For example, step S109 may be performed at least in part by detector 1520. In some embodiments, the monitoring of step S109 may include determining whether or not the arm is in a retroflex position.

Step S113 relates to mode-transition trigger events—i.e. a detectable event whose detection triggers a mode-transition of surgical system 999 from the first mode of step S101 to the second mode of step S121. One example of step S113 is as follows: in response to, and contingent upon a detecting, e.g. by detector 1520, that arm 102 is in a retroflex position, i.e., a detecting that the arm 102 has transitioned from a non-retroflex position to a retroflex position, the surgical system 999 transitions from the first to the second operating mode. As discussed hereinabove, the transition can include an alignment calibration of the surgical arm 102 with an input arm 701.

The transitioning of step S117 may, for example, by triggered by and/or in response to and/or contingent upon detecting that the arm 102 has retroflected, or that an end effector 1530 is in a retroflex position.

A number of embodiments of FIG. 16 are now described. The skilled artisan will appreciate that these embodiments are not required to be mutually exclusive—the embodiments or features thereof may be combined. In some embodiments, not all of the features and/or method steps need be present.

A First Embodiment of FIG. 16

A first embodiments relates to a method of operating a surgical system comprising (i) an input-device array of one or more user-input devices and (ii) an articulated mechanical arm comprising a surgical end effector at a distal end thereof and a plurality of arm joints configured to flex and rotate in response to an electronic control-output from said user-input device, the method comprising: (a) commencing operation of the surgical system in a first operating mode S101 defined with respect to a given single one (e.g. elbow 2103) of the arm joints, wherein the first mode precludes actuation of any arm joint (e.g. including shoulder 2101) of the arm that is not the given single arm joint, and permits controlling the actuation of the single arm (e.g. elbow 2103) joint to cause a flexion of and a rotation of the single arm joint (e.g. elbow 2103); (b) while the surgical system is in the first operating mode (e.g. of S101), (i) retroflexing the distal end of the arm by flexion and rotation of the single arm joint (e.g. elbow 2103), in response to control signals generated by one or more of the user-input devices (e.g. thumbstick 501), so as to bring the end effector 174 to a retroflex operating position, and (ii)monitoring a status (e.g. S109) of the mechanical arm 102 to detect whether or not the arm is in a retroflex position;

(c) in response to and contingent upon (in step S113) detecting that the arm 102 is in a retroflex position, transitioning operation (e.g. 'yes branch' from S113 to S121) of the surgical system from the first mode to a second mode in which the system is enabled to control flexing and rotating of at least one first-mode-precluded arm joint (e.g. elbow 2103) in accordance with respective degrees of freedom of each arm joint; and (d) operating the surgical system in the second mode (e.g. in S121) so as to perform a surgical action using the end effector.

A Second Embodiment of FIG. 16

A method of operating a surgical system comprising (i) first 1510A (e.g. thumbstick 501) and second 1510B (e.g. joystick 701) user-input devices, and (ii) an articulated mechanical arm 102 comprising a plurality of arm joints (e.g. elbow 2103 and shoulder 2101), and a surgical end effector 174 at the distal end of the arm, the method comprising: (a) commencing operation of the surgical system in a retroflexing mode (e.g. first mode of S101) wherein, with respect to flexing and rotation of the arm joints: (i) the first 1510A (e.g. thumbstick 501) user-input device is active to direct flexion and rotation of only a given one of the arm joints, and (ii) the second 1510B (e.g. joystick 701) user-input device is disabled; (b) while in the retroflexing mode by flexion and rotation of the given one (e.g. elbow 2013) of the arm joints, retroflecting a distal portion of the articulated mechanical arm, responsive to electronic control-output from the first user-input device 1510A so as to bring the end effector to a retroflex operating position; (c) transitioning the surgical system from the retroflexing mode to a surgical-operation mode to enable the second user-input device 1510B with respect to flexing and rotating at least one (e.g. shoulder 2101) of the arm joints of the arm other than the given one (e.g. elbow 2103) of the arm joints; and (d) while in the surgical-operation mode, effect flexing and rotating of at least two of the arm joints (e.g. shoulder and elbow) in accordance with respective degrees of freedom of each arm joint, responsive to electronic control-output from the second user-input device 1510B, to thereby move the surgical end-effector to perform one or more surgical actions.

A Third Embodiment of FIG. 16

A method of operating a surgical system that comprises (i) an input-device array 1500 of one or more user-input devices, and (ii) an articulated mechanical arm 102 comprising a plurality of arm joints (e.g. shoulder 2101 and elbow 2103, and a surgical end effector 1764 at a distal end of the arm, the method comprising: (a) commencing operation of the surgical system in a retroflexing mode (e.g. S101) wherein, with respect to flexing and rotation of the arm joints, the input-device array is active to direct flexion and rotation of only a given one (e.g. elbow 2103) of the arm joints; (b) while in the retroflexing mode, retroflecting a distal portion of the articulated mechanical arm by flexion and rotation of the given one of arm joints, responsive to electronic control-output from the input-device array, so as to bring the end effector to a retroflex operating position; (c) transitioning the surgical system from the retroflex mode to the surgical-operation mode to enable the input-device array with respect to flexing and rotating of the arm joints other than the given one of the arm joints; and (d) while in the surgical-operation mode, effect flexing and rotating of at least two (e.b. at least both elbow 2013 and shoulder 2101) of the arm joints in accordance with respective degrees of freedom of each arm joint, responsive to electronic control-output from the input-device array, to thereby move the surgical end-effector to perform one or more surgical actions.

A Fourth Embodiment of FIG. 16

A method of operating a surgical system comprising (i) a user-input device (e.g. joystick 701), and (ii) an articulated mechanical arm 102 comprising a plurality of arm joints, and surgical end effector at a distal end of the arm, the method comprising: (a) commencing operation of the surgical system in a retroflexing mode (e.g. S101) wherein, with respect to flexing and rotation of the arm joints, the user-input device is active to direct flexion and rotation of only a given one (e.g. elbow) of the arm joints; (b) while in the retroflexing mode, retroflecting a distal portion of the articulated mechanical arm by flexion and rotation of the given one of the arm joints, responsive to electronic control-output from the user-input device, so as to bring the end effector to a retroflex operating position; (c) transitioning the surgical system from the retroflex mode to the surgical-operation mode (e.g. 121) to enable the user-input device with respect to flexing and rotating at least one of the arm joints of the arm other than the given one of the arm joints; and (d) while in the surgical-operation mode, effect flexing and rotating of at least two of the arm joints in accordance with respective degrees of freedom of each arm joint, responsive to electronic control-output from the user-input device, to thereby move the surgical end-effector to perform one or more surgical actions.

A Fifth Embodiment of FIG. 16

A method of using a surgical system, the method comprising: (a) providing an articulated mechanical arm capable of displacing a surgical end effector 174 at a distal end thereof, the arm comprising a plurality of arm segments connected (e.g. serially) by a corresponding plurality of arm joints (e.g. elbow and shoulder) configured to flex and rotate in response to an electronic control-output from a user-input device; (b) maneuvering the end effector to a retroflex operating position while operating in a first input mode in which a displacement of an input device (e.g. 1510A such as thumbstick) or of a displaceable portion thereof is translated to a speed of a flexion and/or of a rotation of an arm joint; (c) in response to and contingent upon detecting that the end effector is in the retroflex operating position, transitioning from operating in the first input mode to operating in a second input mode in which a displacement of an input device (e.g. 1510B such as joystick) or of a displaceable portion thereof is translated to a corresponding displacement of at least one arm segment; and (d) after the transitioning and while operating in the second input mode, performing a surgical action using the end effector.

Figure 22A:
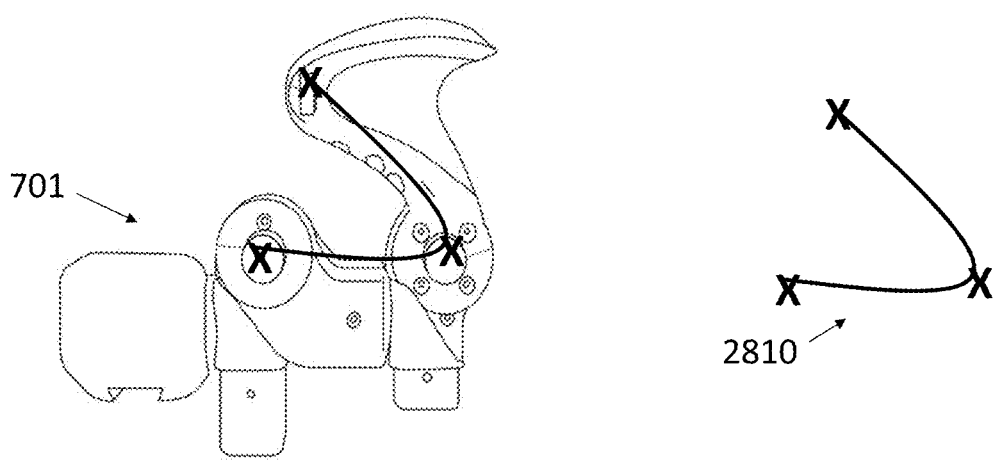
FIG. 22A schematically shows a user-input device having a given curve-shape, according to embodiments of the present invention.
Figure 22B:
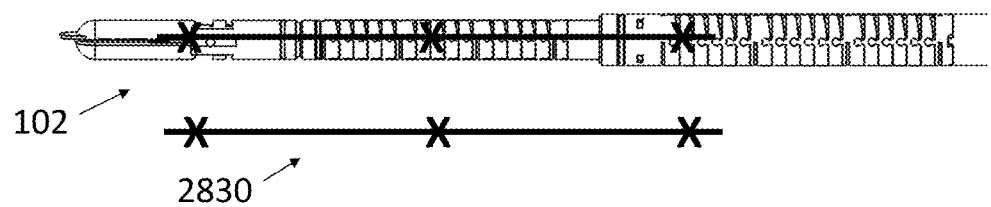
FIG. 22B schematically shows a surgical arm at a first time, having a curve-shape that does not match the given curve-shape of FIG. 22A.
Figure 22C:
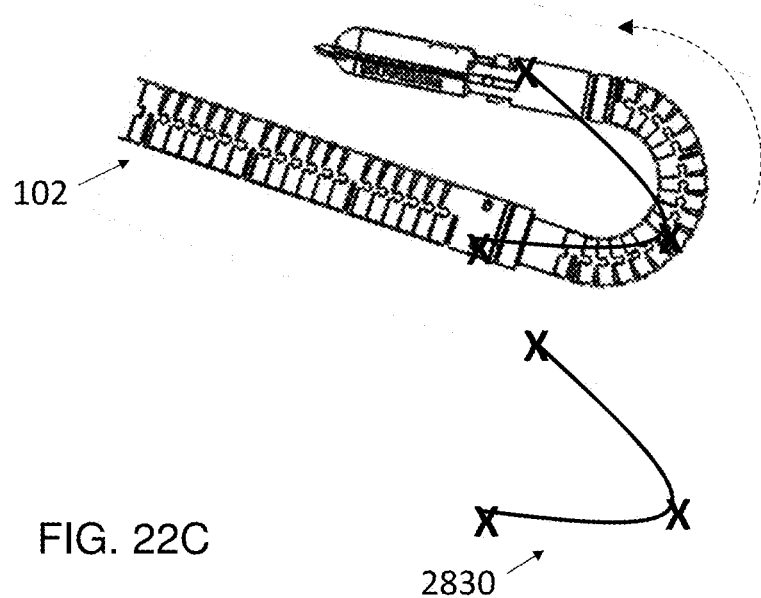
FIG. 22C schematically shows a surgical arm at a second time, having a curve-shape that matches the given curve-shape of FIG. 22A.

Specific Embodiments of FIG. 16 Relating to FIGS. 22A-C (A) A method of operating a surgical system comprising (i) a given user-input device (e.g., an articulated and/or flexible user-input device—e.g. joystick 701) and (ii) an articulated mechanical arm 102 comprising a surgical end effector at 174 a distal end thereof and a plurality (e.g. shoulder 2101 and elbow 2103) of arm joints configured (e.g. in at least one operating mode of the surgical system) to flex and rotate in response to an electronic control-output from the (e.g. articulated and/or flexible) given user-input device 1510B (e.g. joystick 701) (e.g. and optionally also in response to output from one additional user-input device 1510A (e.g thumbstick 501) other user-input device other than the given user-input device), the method comprising: a. commencing operation of the surgical system in a first operating mode (e.g. where motion of the arm is not controlled by and/or insensitive to output of the given user-input device 1510B); b. while the surgical system is in the first operating mode (e.g. of step S101), (i) modifying a curve-shape of the arm (e.g. starting from 2830 of FIG. 22B) by mechanized flexion and/or by rotation of one or more the arm joints of the articulated mechanical arm, and (ii) monitoring a shape-status of said mechanical arm to detect whether or not a portion or entirety thereof arm has a curve-shape that matches (e.g. the curves match or 2D projections thereof match) a currently-prevailing curve-shaped (e.g. shape 2810) defined by the (e.g. articulated and/or flexible) given user-input device 1510B and/or a resting-state curve (e.g. shape 2810) defined by the (e.g. articulated and/or flexible) given user-input device 1510B; c. in response to and contingent upon positive detecting of a match (i.e. 'positive' detecting is a detecting that there is a match between the curve-shapes defined by the arm and the given-user input-device) [i.e. in FIG. 22B there is no match between 2830 and 2810 but in FIG. 22C where there is a match therebetween), transitioning operation of the surgical system from the first mode (e.g. of step S101) to a second mode (e.g. of step S121); d. responsive to output of the (e.g. articulated and/or flexible) given user-input device (e.g. 1510B—e.g. joystick), operating the surgical system in the second mode (e.g. (e.g. control) output of the given user-input device modifies a configuration of the arm or a section (e.g. non-distal section)) or an element of the arm (e.g. any joint thereof)) so as to perform a surgical action using the end effector.

(B) A method of operating a surgical system comprising (i) a user-input device (e.g., an articulated and/or flexible user-input device) (e.g. controlled by a user-input device having position control) and (ii) an articulated mechanical arm comprising a surgical end effector at a distal end thereof and a plurality of arm joints configured (e.g. in at least one operating mode of the surgical system) to flex and rotate in response to an electronic control-output from the (e.g. articulated and/or flexible) given user-input device (e.g. an optionally also in response to output from one additional user-input device other user-input device other than the given user-input device), the method comprising: a. commencing operation of the surgical system in a first operating mode (e.g. where motion of the arm is not controlled by and/or insensitive to output of the given user-input device); b. while the surgical system is in the first operating mode, (i) modifying a curve-shape of the arm by mechanized flexion and/or by rotation of one or more the arm joints of the articulated mechanical arm, and (ii) monitoring a shape-status of said mechanical arm to detect whether or not a portion or entirety thereof arm has a curve-shape that matches (e.g. the curves match or 2D projections thereof match) a pre-defined curve shape (e.g. having one or more local minimum or local maximum; having one or more inflection points—e.g. an S curve shape); c. in response to and contingent upon positive detecting of a match, transitioning operation of the surgical system from the first mode to a second mode; d. responsive to output of the (e.g. articulated and/or flexible) given user-input device, operating the surgical system in the second mode (e.g. (e.g. control) output of the given user-input device modifies a configuration of the arm or a section (e.g. non-distal section)) or an element of the arm (e.g. any joint thereof)) so as to perform a surgical action using the end effector.

Additional Features Relating to the Specific Embodiments of FIG. 16

One or more of (e.g. in any combination) of the following may be provided:

(1) the transitioning step of step c comprises handing off user-control of a configuration of the arm from a different user-input device (e.g. 1510A—e.g. a thumbstick device) other than the given user-input device (e.g. 1510B—for example joystick) to the given user-input device (e.g. 1510B—for example joystick).

(2) the method further comprising concurrent with or subsequent and while the surgical system is in the second mode (e.g. of step S121), a configuration of the arm 102 is controlled by output of the user control device (e.g. 1510A—e.g. a thumbstick device) such that a magnitude of a displacement of the given input device or of a displaceable portion thereof is translated to a corresponding displacement of at least one portion of the arm and/or of at least one arm segment of the arm.

(3) the method further comprising concurrent with or subsequent to step (d) (e.g. S121) and while the surgical system is in the second mode, a configuration of the arm is controlled by output of the user control device (e.g. 1510B—e.g. joystick 701) such that a magnitude of a displacement of the given input device or of a displaceable portion specifies (e.g. completely specifies; e.g. commands) a destination position of an arm element (i.e. different from a currently prevailing position) and/or a destination configuration (e.g. different from a currently prevailing configuration) of the arm.

(4) the first mode is: (i) defined with respect to a proper subset of the plurality of the arm joints (e.g. only elbow 2103); (ii) precludes actuation, by control signals from the articulated user-input device, of one or more arm joint(s) (e.g. shoulder 2101) of the arm that is(are) not a member of the proper subset of joints, and (iii) permits controlling the actuation of the arm joint(s) (e.g. elbow 2103) belonging to the proper subset to cause a flexion of and/or a rotation of the each arm joint of the proper subset.

(5) upon transitioning from the first to the second mode, the articulated user-input device (e.g. 1510B—e.g. joystick 701) is enabled to control flexing and rotating of at least one first-mode-precluded arm joint (e.g. 703 of joystick 701).

(6) the modifying of the shape of arm 102 is performed responsive to electronic control-signals provide by the given user-input device (e.g. 1510B—e.g. joystick).

(7) the modifying of the shape of arm is performed responsive to electronic control-signals provide by a user-input device other than the given user-input device.

(8) the modifying of the shape of arm is performed automatically (e.g. automated retroflexing).

(9) (i) in the first mode the arm-shape is controlled by the articulated input device or another input device operating such that displacement of an input device or of a displaceable portion thereof is translated to a speed of a flexion and of a rotation of an arm joint; and (ii) in the second mode the arm-shape is controlled by the articulated input device operating such that a displacement of articulated input device or of a displaceable portion thereof is translated to a corresponding displacement of at least one arm segment.

Discussion of FIGS. 17-21

In an example, a first mode and a second mode both use the same input device, an avatar-like input arm. The input arm is used in a restricted mode for retroflecting the arm as explained hereinabove, at which point a transition is made to fully enabled use in the second mode. However, at this point, the input arm, or at least a handle member (e.g., handle member 702 of FIG. 10) may have been flipped around by as much as 180° or more than 180° in accordance with the angle of flexion employed in the retroflexion. This means that (a) the handle 702 is uncomfortably 'upside down' from the perspective of the surgeon, and (b) the coordinate system used by the surgical system is 'backwards'. The surgeon's perspective has switched from looking 'distally' to retroflex the arm, to looking 'proximally' to perform a surgery with arm in a retroflex position, and as a result a displacement vector or reorientation arc of a segment member is not translated to a corresponding (e.g., parallel) displacement vector or reorientation arc in the same x-y-z space.

It should be noted that the exemplary design of the input device 701 and handle member 702 is provided for illustrative purposes, while in other examples and in other embodiments, input devices and handle members can be designed and implemented in different ways. For example, in some embodiments a handle member can be physically detached from an input device of which it is functionally a part. As another example, in some embodiments, an avatar-like or joystick-like input device be wholly or almost wholly or mostly comprised of a hand-operated and/or hand-graspable handle member. As another example, in some embodiments, a handle member can incorporate multiple operating functions in its design by including, and not exhaustively, buttons, switches, toggles, wheels, knobs, and/or small sticks such as thumbsticks so as to 'combine' multiple input devices and their respective functions into what appears visually to be a single input device. The repeated presentation herein of the input device 701 and handle member 702 of FIG. 10 is for convenience and easier comprehension, and should not be understood as a limitation of input device and handle member design.

It is now disclosed that transitioning from a first input device of an array of one or more input devices to a second input device of the array when transitioning from the first mode to the second mode can overcome the aforementioned shortcomings. The handle member 702 of the second input device (the avatar-like input arm 701) can be placed in advance in an orientation that is not 'upside down' from the surgeon's perspective; the retroflexing can performed with an input device (e.g., input device 501/405), the use of which does not include or require that the handle member 702 of the second input device be moved, or if moved then not moved more than the 90° that might be a 'tipping point' to becoming 'upside down' from the surgeon's perspective. Moreover, the control circuitry controlling the second input device (the input arm 701) can be set (e.g., programmed) to use a 'direct' coordinate translation matrix, one in which a displacement vector of a segment member of the input arm is translated to a corresponding (e.g., parallel or, at minimum, retaining the same sign in each of the x, y and z directions or at least two out of three directions) displacement vector of the corresponding surgical arm segment, and/or in which a reorientation arc of a segment member of the input arm is translated to a corresponding reorientation arc of the corresponding surgical arm segment.

It can therefore be desirable, in some embodiments, to ensure a handoff (transition) from a first mode to the second mode, in which control of arm movement transfers from a first input device (such as the 'thumbsticks' detailed hereinabove) to an avatar-like input arm, that ensures ergonomic comfort and convenience based on the optimally oriented handle member and directly translatable (input arm to surgical arm) coordinate translation matrix.

Figure 17:
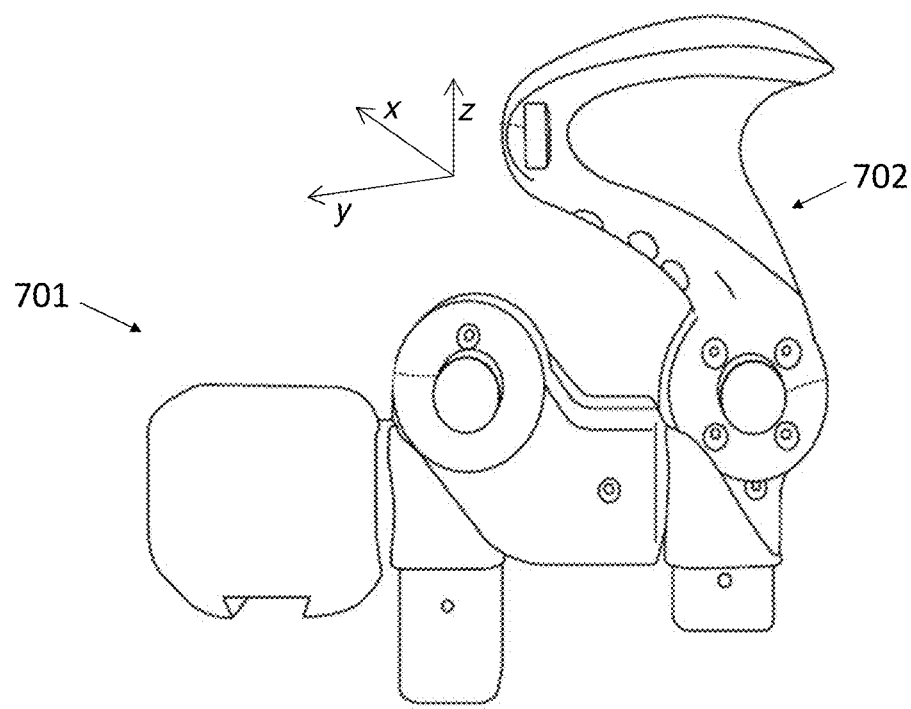
FIG. 17 is a schematic illustration of a user-input device oriented in a first given x-y-z space, according to embodiments of the present invention.
Figure 18:
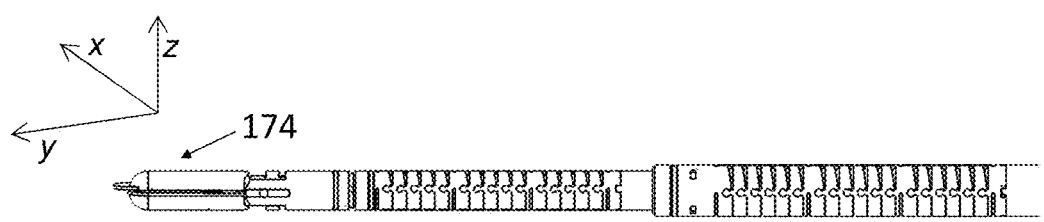
FIG. 18 is a schematic illustration of a portion of a surgical arm oriented in the first given x-y-z space of FIG. 17, according to embodiments of the present invention.

Referring now to FIG. 17, a user-input device 701 is oriented in an x-y-z space that corresponds to the same x-y-z space in which an arm 102, or at least a distal portion thereof, is oriented in FIG. 18. The arm 102 of FIG. 18, which an end effector 174 connected at the distal end of the arm 102, is shown as not flexed, indicating an orientation of an arm at the beginning, or prior to, a surgical operation. Controlling the arm 102 and positioning the end effector 174 in FIGS. 17-18 is straightforward; leftwards displacement of the input device 701 translates to leftwards displacement of the arm 102 (e.g., along the x-axis), forward translates to forward (e.g., along the y-axis), rightwards means rightwards (again, along the x-axis), and backwards translates backwards (again, along the y-axis). Upwards displacement of the input device 701 translates to upwards displacement of the arm 102 (e.g., along the z-axis) and downwards translates to downwards.

Figure 19:
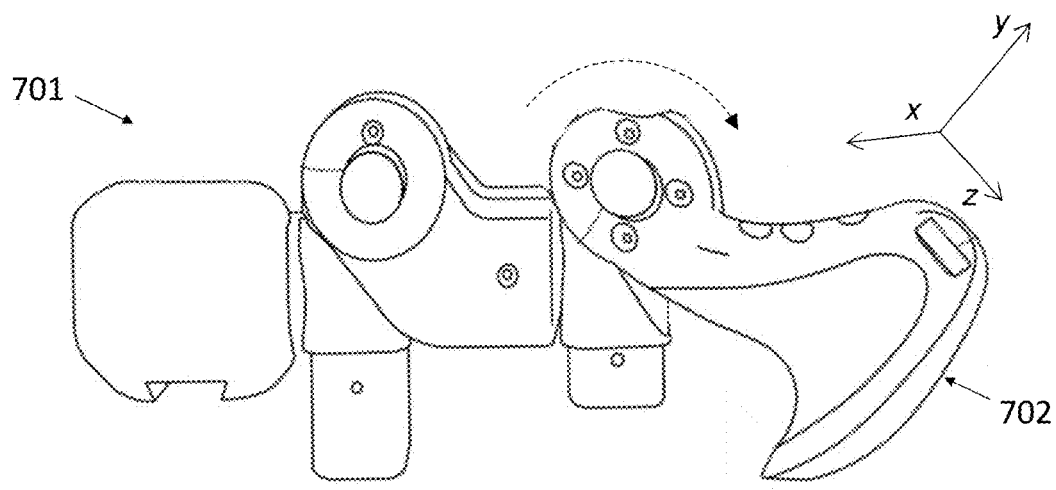
FIG. 19 is a schematic illustration of a user-input device with a handle member re-positioned to be oriented in an x-y-z space that is not the first given x-y-z space of FIG. 17, according to embodiments of the present invention.
Figure 20:
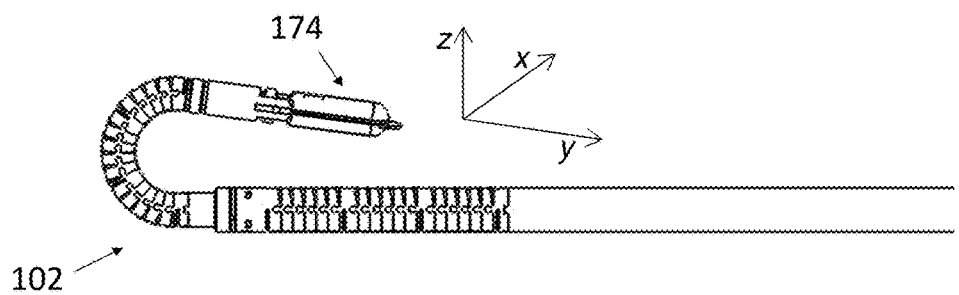
FIG. 20 is a schematic illustration of the surgical arm of FIG. 18, retroflected in the first given x-y-z space of FIG. 17, according to embodiments of the present invention.

In FIGS. 19 and 20, the distal portion of the arm 102 is retroflected, placing the arm (and the attached surgical end effector 174) in a retroflex position. The handle member 702 of the user-input device 701 has been rotated in order to effect the retroflexing movement of the arm 102. If one were to transition at this point to a surgical-operation mode, the user-input device 701 would be oriented in the rotated x-y-z coordinate system of FIG. 19, which does not match the x-y-z coordinate system of the end-effector 174 in FIG. 20 (which has rotated in accordance with the retroflecting of the arm 102 and now matches the retroflex orientation/position of the end effector 174). Note: the x-y-z coordinate system of the retroflex arm 102 has 'flipped' so as to match what in typical surgical systems is the surgeon's perspective. For example, if a camera, e.g., an endoscopic camera at the end of an arm, does not 'flip', then the surgeon cannot see the surgical workspace or see whatever needs to be seen. However, the flipped handle 702 and 'flipped' (retroflected) end effector no longer orient in a shared three-dimensional x-y-z space. As discussed, hereinabove, there are two choices available at this point: either grasp the device 701 from a different perspective in a different manner than is usually taken, or perform surgical operations such that motions of the input device 701 (specifically, of the handle member 702) do not ergonomically translate easily to the surgical arm 102 in the same x-y-z coordinate system. For example, a leftward displacement of the device 701 of FIG. 19 (according to its x-y-z coordinate system) would result in a rightward displacement of the end effector 174 according to its x-y-z coordinate system, while up would mean down and so on.

As previously discussed, a first solution to the 'flipped handle' is to use a different user-input device for the retroflecting of the arm. This results in an un-flipped handle such as that shown in FIG. 17 controlling, in a subsequently assumed post-transition surgical-operation mode, the arm and end effector such as are shown in FIG. 20. The skilled artisan will understand that the x-y-z coordinate systems appear to be the reverse of each other, but in actuality align the input device 701 and the arm 102 such that a leftwards displacement (e.g., of the device 701 in the surgeon's hand) translates to a leftwards displacement of the end effector 174 (from the perspective of the surgeon), and so on in all the directions of the shared x-y-z coordinate system—unless, for example, the surgeon can grasp the handle member from the opposite direction.

Figure 21:
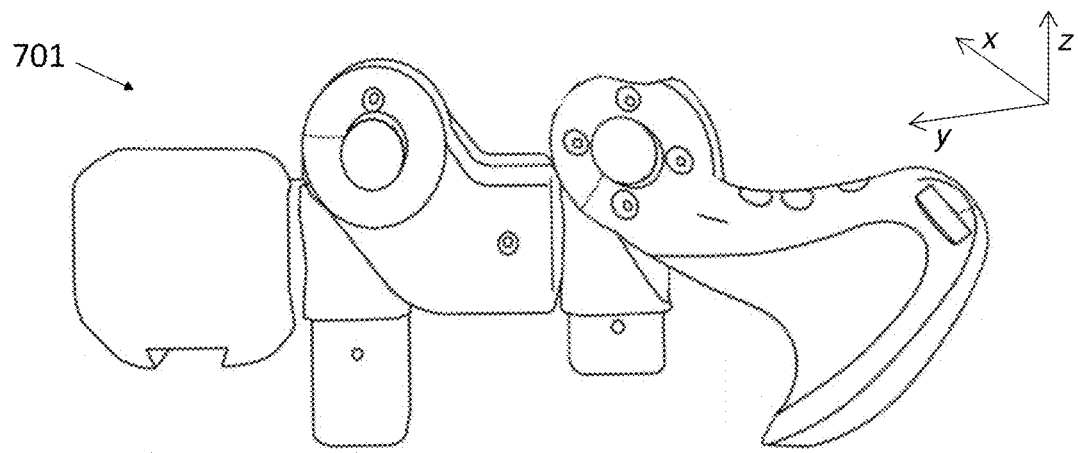
FIG. 21 is a schematic illustration of the user-input device of FIG. 19, oriented in the first given x-y-z space of FIG. 17, according to embodiments of the present invention.

A second solution to the 'flipped handle' is illustrated in FIG. 21. As previously discussed, the handle member 702 of FIG. 19 has been flipped, i.e., rotated, so as to rotate the x-y-z coordinate system of the input device 701. According to embodiments, the exemplary surgical system of the second solution is configured to change the orientation of the x-y-z coordinate system of the input device 701. In other words, the same input device 701 is used in a first retroflexing mode in the x-y-z space shown in FIG. 17. That x-y-z space is rotated in FIG. 19 (due to the 'flipped handle'), making the input device 701 difficult to use in the second surgical-operation mode (e.g., left is right, up is down, etc.). Therefore the surgical system replaces the original but flipped x-y-z coordinate system of FIG. 19 with a new x-y-z coordinate system in FIG. 21—which appears to match the original x-y-z coordinate system of FIG. 17, but it is now navigable not by an input device oriented as in FIG. 17 but by the flipped-handle input device as oriented in FIG. 21.

We now refer to FIGS. 22A-C, which has already been discussed hereinabove with respect to certain embodiments of FIG. 16. FIG. 22A shows an input device 701 having a curve shape 2810. At a first time T1, the corresponding arm 102 has an unflexed shape shown in FIG. 22B. The arm 102 has a curve-shape 2830 which clearly does not match the curve shape 2810 of the input device 701 at Time=T1. After manipulating the arm 102 with a different user-input device (not shown in FIGS. 22A-C), the arm 102 is retroflected prior to Time=T2, as shown in FIG. 22C. At this point the curve-shape 2830 of the arm 102 matches the curve shape 2810 of the input device 701. When this match is detected the surgical system, as described earlier in the discussion of FIG. 16, can transition from a first (retroflexing) mode to a second (surgical-operation) mode with the device 701 and end-effector 174 oriented in the same x-y-z coordinate system, e.g., as shown in FIGS. 20-21.

FIGS. 22A-C show a retroflexed arm as a non-limiting example of a curve-shape that is to be matched between the surgical arm and the user-input device. In other examples, the curve-shape to be mapped can include any useful curve-shape of a surgical arm. Two illustrative examples of useful arm shape-curves can be seen in FIGS. 4 and 5, which are discussed hereinabove.

First Additional Discussion

Figure 23A:
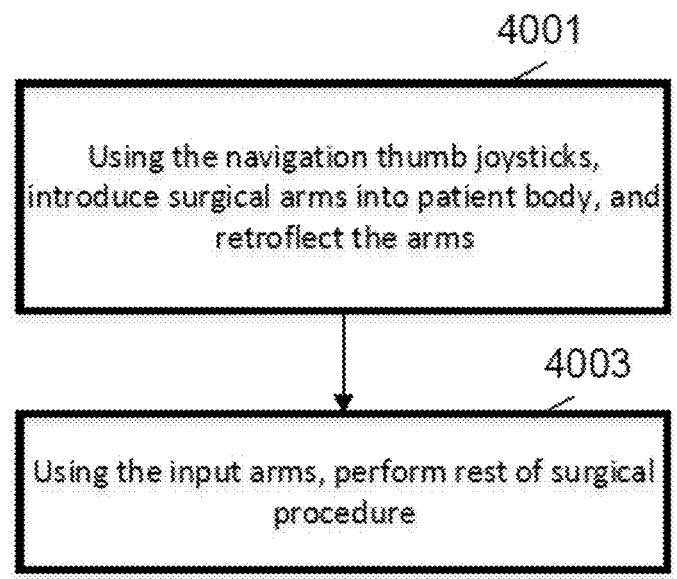
FIG. 23A shows a flowchart of a method for dual control of surgical arms, according to embodiments of the present invention.
Figure 23B:
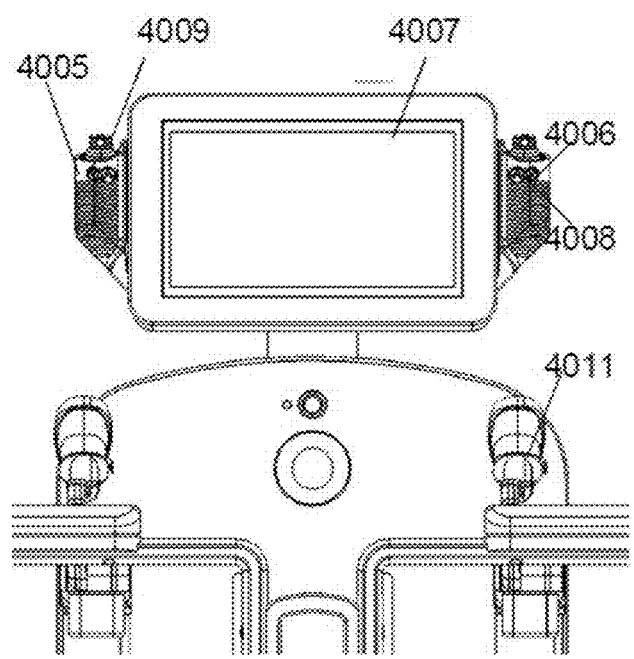
FIGS. 23B and 23C are schematic illustrations of control consoles comprising dual control means, according to embodiments of the present invention.
Figure 23C:
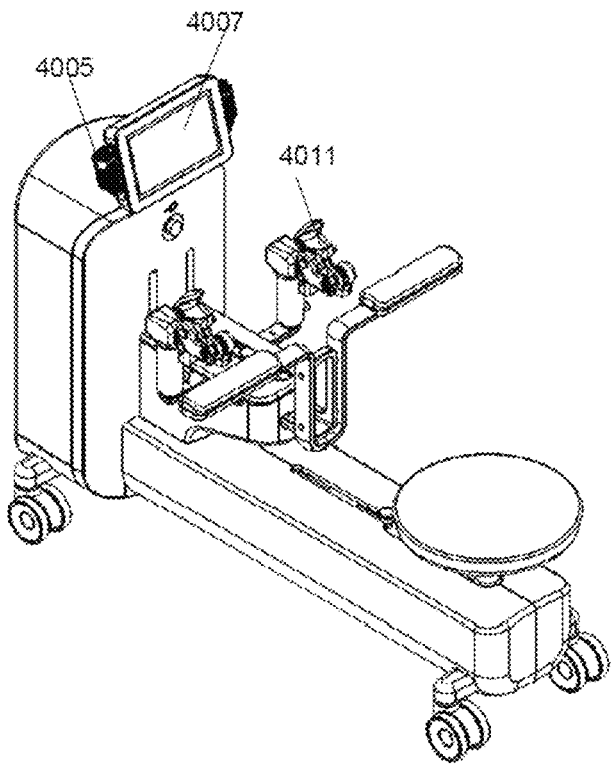

We now refer to FIGS. 23A-C.

In some embodiments, control of the one or more surgical arms is achieved via one or more input arms, joysticks, control handles, and/or other means suitable for manipulation by a user (e.g. a surgeon) which is then translated into a matching articulation of the surgical arm(s).

In the example described herein, as referred to in the flowchart of FIG. 23A, some embodiments include dual-control of the surgical arms. In some embodiments, a first user input (in this example, thumbsticks 4005 of FIG. 23B) is used for introducing the surgical arms into the patient body, for example through the vagina, and then for retroflecting the surgical arms (4001). In some embodiments, retroflecting (for example, bending backwards) of the surgical arms within the patient body is performed to reduce an area within which the surgical arm is located. Optionally, retroflecting is performed during a surgical procedure to avoid obstacles such as certain organs or portions thereof, for example, an inner wall of the abdomen. Optionally, retroflecting is performed to position the surgical arms at an orientation in which a laparoscopic surgeon is familiar with, for carrying out the operation.

In some embodiments, a second user input, in this example in the form of input arms 4011 (e.g. avatar joysticks) is then used for performing the rest of the surgical procedure (4003).

In some embodiments, thumbsticks 4005 are positioned adjacent the control console screen 4007, for example on opposing sides of the screen. In some embodiments, each of the thumbsticks 4005 comprises a nipple type controller 4009 shaped and sized for the user's thumb. In some embodiments, the nipple of the thumbsticks is at rest position when centered, and is configured to spring back to the rest position upon release of the thumb. In some embodiments, the extent of movement of the nipple relative to its central rest position determines a resulting velocity of the surgical arm movement. For example, the further the nipple is pushed away from its central rest position, the higher the velocity of the movement of the surgical arm (and vice versa—the closer the nipple is to its central rest position, the lower the velocity of the arm).

In some embodiments, when controlling the surgical arms via the thumbsticks, one or more of the surgical arm joints (e.g. a shoulder joint, a wrist joint) are restricted from movement. In some embodiments, all surgical arm joints except an elbow joint are prevented from moving, and only flexion and/or rotation of the elbow joint are enabled. In some embodiments, linear movement of the surgical arm (as a single body) is also enabled, for example to advance or retract the arm. In some embodiments, movement of the nipple actuates flexion and/or rotation of the elbow joint. In some embodiments, linear movement of the arm is actuated by separate actuators, for example using push buttons such as 4006, 4008, configured for example along a body of the thumbstick 4005. In an example, button 4006 advances the surgical arm distally (e.g. into the abdomen); button 4008 retracts the surgical arm proximally.

In some embodiments, during use of the thumbsticks, the input arms 4011 are locked at a rest position, for example by solenoid locks. In some embodiments, the rest position of the input arms is selected as the retroflected position. Optionally, this position allows the surgeon to continue the procedure directly following retroflection using the thumbsticks. In some embodiments, when the input arms are operated, operation of the thumbsticks is disabled.

A potential advantage of using the thumbsticks for navigation into the body and for retroflecting the surgical arms while selected arm joints such as the shoulder joint remain stationary may include reducing a bending radius of the surgical arm, thereby reducing a likelihood of encountering surrounding obstacles such as the inner abdominal wall. Another potential advantage of using the thumbsticks for navigation and/or retroflection processes may include improved control over the surgical arms, for example as compared to navigating and retroflecting with the input arms in which the ergonomics of the handle may be less suitable for supporting the rotational movement that the surgeon needs to perform while holding the handle in order to carry out retroflection.

In some embodiments, during introducing of the surgical arms into the body the surgical arms are straight (optionally to provide for insertion via a cannula), while the input arms are at a rest, locked, retroflected position. Optionally, following retroflection of the surgical arms using the thumbsticks, the surgeon releases the thumbsticks and moves their hands to the input arms. Once the input arms are grasped and optionally lifted by the surgeon, control over the surgical arms is automatically gained, and the surgeon may continue the procedure using the input arms. In some embodiments, when one or more input arm joints are locked by solenoid locks, lifting of the input arm by the surgeon automatically releases the solenoid locks. Additionally or alternately, manual locks of the input arm joints are released, for example via a sensor that detects an input arm position.

In some embodiments, the system (e.g. a system processor) is configured to recognize one or more positions of the input arms, for example when the input arms are at their rest position, and optionally display to the current position to the user.

Figure 24:
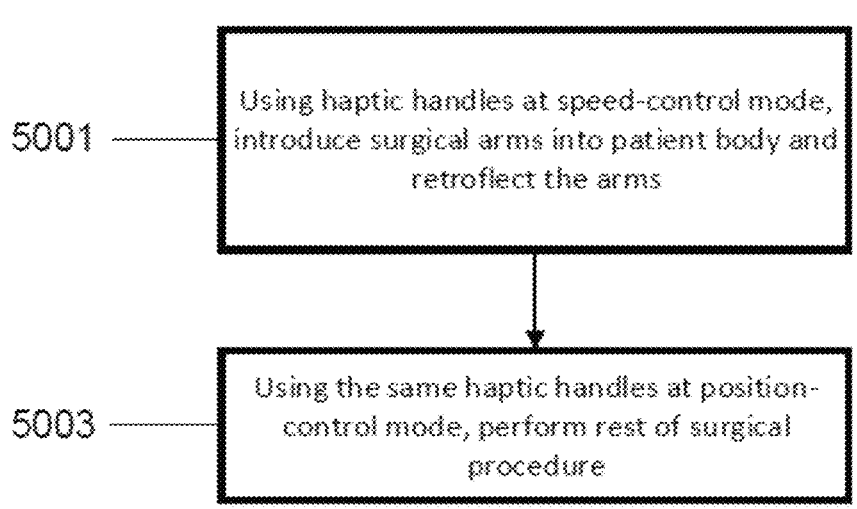
FIG. 24 is a flowchart of a method of using haptic handles to control one or more surgical arms, according to embodiments of the present invention.

We now refer to FIG. 24. In some embodiments, haptic handles which provide force feedback to the user (a suitable example of which being the 'omega.7' haptic device available from Force Dimension of Nyon, Switzerland) are used throughout the operation for controlling movement and articulation of the surgical arms. In some embodiments, the haptic handles are set to provide counter resistance for preventing the user from moving in directions that are not supported by the surgical arm, for example bending the elbow joint of the surgical arm backwards; touching a joint (e.g. an elbow joint) with a different segment of the same arm; and/or other. In some embodiments, the handles are set to provide counter resistance which varies in accordance with a current anatomical position and/or orientation of the surgical arms. In an example, resistance may be increased if the user attempts a disallowed anatomical area, such as an organ that should be avoided.

In some embodiments, the haptic handles are programmed to operate according to various control modes. Optionally, the control mode is selected in accordance with a current stage in the surgical operation. In some embodiments, switching between different modes is performed via one or more of a screen interface, one or more buttons on the control console or handles, a foot pedal, and/or other.

In some embodiments, during a first stage of the procedure, during which the surgical arms are introduced into the patient body and optionally retroflected, the haptic handles are used in "speed—control" mode (5001). Optionally, in the speed-control mode, relative movement of a handle with respect to the handle rest position sets the speed in which the surgical arm is moved. As the user moves the handle further away from the rest position, the speed is raised, and vice versa. For example, movement of the handle to the right of its rest position may result in rotation of an arm joint (e.g. elbow joint) to the right, at a speed determined according to the distance of the handle from its rest position. In some embodiments, in the speed-control mode, the haptic handles are set to provide an elastic (spring-like) counter resistance to the movement of the user. In some embodiments, in the speed control mode, a control algorithm is applied, converting a current configuration of the haptic handle into speed commands issued to the actuators (e.g. motors) of the surgical arm, such as to increase a rotation speed of one or more motor gears.

A potential advantage of using the speed control mode during introducing and optionally retroflecting the surgical arms in the body may include that during retroflecting the directions are reversed (e.g. upwards/downwards), yet that change can be ignored and the motion can be naturally continued, since the resulting movement of the surgical arms is limited and what changes is the speed of movement.

In some embodiments, during a second stage of the surgical procedure, optionally during the rest of the procedure, the haptic handles are set to "position-control" mode (5003). Optionally, in the position control mode, a spatial position of the handles sets a respective position of the surgical arms. In the position control mode, a user's displacement of the haptic handle is translated to a relative displacement command to the surgical arm. In some embodiments, converting the displacement of the haptic handle is controlled according to an algorithm. In some embodiments, control is according to known algorithms (e.g. the Inverse Jacobian algorithm). Additionally or alternatively, in some embodiments, control is according to custom algorithms. In an example, a custom algorithm is set to scale the user's motion, such as to increase accuracy of movement. Such scaling may include amplifying the movement required on the user end by a selected coefficient to produce a similar non-amplified movement of the surgical arm. For example, the for the arm to move a distance X, the user will need to move the handle by A*X (A>1). In another example, an algorithm is selected to filter signals, for example filtering using a low-pass filter to reduce user hand tremors.

In some embodiments, in the position control mode, a clutch mechanism is provided, allowing a user to temporarily disconnect from the surgical arm (such that movement of the input haptic handle no longer controls the surgical arm). Optionally, when disconnected, the user may freely re-position the haptic handle. In an example, the user re-positions the haptic handle to a position and/or orientation in which it is more comfortable for the user to carry out and control the next movement.

In some embodiments, the extent of resistance sensed by the user in response to movement of the handles is selected and controlled. In an example, a floating mode is set, in which the user substantially does not encounter resistance and is free to move the handle in all directions. Additionally or alternatively, a level of resistance sensed by the user is adjusted, for example so that the user senses a high resistance in response to one movement and a low or no resistance in response to another movement.

In some embodiments, the amount of resistance is controlled based on the anatomical location of the surgical arms. For example, a high resistance may be set where obstacles (e.g. the abdominal wall) are found near the surgical arm. In a specific example, if an obstacle is found on the right of the surgical arm, the user may encounter high resistance in response to moving the handle to the right; if no obstacles are found on the left of the arm, the user may encounter low or no resistance in response to moving the handle to the left. Optionally, the extent of resistance is defined by setting system definitions such as producing wall type resistance, rubber like resistance, sand type resistance and/or other.

Second Additional Discussion

A method is disclosed, according to embodiments, for operating a surgical system comprising (i) an articulated mechanical arm comprising a plurality of arm joints, and (ii) first and second user-input devices for controlling the arm, and (iii) a surgical end effector at the distal end of the arm. The method comprises: (a) commencing operation of the surgical system in a retroflexing mode wherein, with respect to flexing and rotation of the arm joints: (i) the first user-input device is active to direct flexion and rotation of only a given one of the arm joints, and (ii) the second user-input device is disabled; (b) while in the retroflexing mode, retroflecting a distal portion of the articulated mechanical arm by flexion and rotation of the given one of the arm joints, responsive to electronic control-output from the first user-input device so as to bring the end effector to a retroflex operating position; (c) transitioning the surgical system from the retroflexing mode to a surgical-operation mode to enable the second user-input device with respect to flexing and rotating at least one of the arm joints of the arm other than the given one of the arm joints; and (d) while in the surgical-operation mode, effect flexing and rotating of at least two of the arm joints in accordance with respective degrees of freedom of each arm joint, responsive to electronic control-output from the second user-input device, to thereby move the surgical end-effector to perform one or more surgical actions.

In some embodiments, the surgical system can additionally comprise control circuitry effective, while the surgical system is in the retroflexing mode, to restrict the actuation of arm joints other than the single arm joint.

In some embodiments, the transitioning can include calibrating the input device with respect to at least one of a position and an orientation of the end effector or of a distal portion of the arm.

In some embodiments, it can be that the first input device is configured for controlling actuation of the single arm joint and/or is not configured for controlling actuation of arm joints other than the single arm joint.

In some embodiments, the transitioning to the surgical-operation mode can be in response to and/or contingent upon detecting that the arm is in a retroflex position.

A surgical system according to embodiments comprises: (a) an articulated mechanical arm comprising a plurality of arm joints, and a surgical end effector at a distal end of the arm; and (b) first and second user-input devices for controlling the arm, wherein the surgical system is configured to operate, asynchronously, in (i) a retroflex mode in which a distal portion of the articulated mechanical arm is operative to be retroflected, responsive to electronic control-output from the first user-input device, so as to bring the end effector to a retroflex operating position, and in (ii) a surgical-operation mode in which at least two of the arm joints are operative to be flexed and rotated, responsive to electronic control-output from the second user-input device, so as to thereby move the surgical end-effector to perform one or more surgical actions, such that: (A) while in the retroflexing mode, with respect to flexing and rotation of the arm joints, the first user-input device is active to direct flexion and rotation of only a given one of the arm joints, and the second user-input device is disabled, and (B) while in the surgical-operation mode, the second user-input device is enabled with respect to flexion and rotation of at least one of the arm joints of the arm other than the given one of the arm joints, in accordance with respective degrees of freedom of each arm joint.

In some embodiments, the surgical system can additionally comprise control circuitry effective, while the surgical system is in the retroflexing mode, to restrict the actuation of arm joints other than the single arm joint.

In some embodiments, the surgical system can be configured such that transitioning includes calibrating the input device with respect to at least one of a position and an orientation of the end effector or of a distal portion of the arm.

In some embodiments, it can be that the first input device is configured for controlling actuation of the single arm joint and/or is not configured for controlling actuation of arm joints other than the single arm joint.

In some embodiments, the surgical system can be configured such that the transitioning to the surgical-operation mode can be in response to and/or contingent upon detecting that the arm is in a retroflex position.

A method is disclosed, according to embodiments, of operating a surgical system. According to the method, the surgical system comprises (i) a user-input device, and (ii) an articulated mechanical arm comprising a plurality of arm joints, and surgical end effector at a distal end of the arm. The method comprises: (a) commencing operation of the surgical system in a retroflexing mode wherein, with respect to flexing and rotation of the arm joints, the user-input device is active to direct flexion and rotation of only a given one of the arm joints; (b) while in the retroflexing mode, retroflecting a distal portion of the articulated mechanical arm by flexion and rotation of the given one of the arm joints, responsive to electronic control-output from the user-input device, so as to bring the end effector to a retroflex operating position; (c) transitioning the surgical system from the retroflex mode to the surgical-operation mode to enable the user-input device with respect to flexing and rotating at least one of the arm joints of the arm other than the given one of the arm joints; and (d) while in the surgical-operation mode, effect flexing and rotating of at least two of the arm joints in accordance with respective degrees of freedom of each arm joint, responsive to electronic control-output from the user-input device, to thereby move the surgical end-effector to perform one or more surgical actions.

In some embodiments of the method, the surgical system can additionally comprise control circuitry effective, while the surgical system is in the retroflexing mode, to restrict the actuation of arm joints other than the given one of the arm joints. In some such embodiments, the restricting can be by disabling actuation of arm joints of the arm other the given one of the arm joints.

In some embodiments, the user-input device can control the actuation of the plurality of arm joints in both the retroflexing mode and the surgical-operation mode.

In some embodiments, the user-input device can be precluded from generating or transmitting control outputs that would control actuation of arm joints of the arm other than the given one of the arm joints.

In some embodiments, the transitioning to the surgical-operation mode can be in response to and/or contingent upon detecting that the arm is in a retroflex position.

In some embodiments, the transitioning can includes calibrating the user-input device with respect to at least one of a position and an orientation of the end effector or of a distal portion of the arm.

In some embodiments, the method can additionally comprise, following the operating in the second mode, unflexing the distal end of the arm, so as to bring the arm to an unflexed position.

A surgical system is disclosed according to embodiments, comprising: (a) a user-input device; and (b) an articulated mechanical arm comprising (i) a plurality of arm joints and (ii) a surgical end effector at a distal end of the arm, wherein the surgical system is configured to operate, asynchronously, in (A) a retroflexing mode in which a distal portion of the articulated mechanical arm is retroflected, responsive to electronic control-output from the user-input device, so as to bring the end effector to a retroflex operating position, and in (B) a surgical-operation mode in which at least two of the arm joints are flexed and rotated, responsive to electronic control-output from the user-input device, so as to thereby move the surgical end-effector to perform one or more surgical actions, such that (A) while in the retroflexing mode, with respect to flexing and rotation of the arm joints, the user-input device is active to direct flexion and rotation of only a given one of the arm joints, and (B) while in the surgical-operation mode, the user-input device is enabled with respect to flexion and rotation at least one of the arm joints of the arm other than the given one of the arm joints, in accordance with respective degrees of freedom of each arm joint.

In some embodiments, the surgical system can additionally comprise control circuitry effective, while the surgical system is in the retroflexing mode, to restrict the actuation of arm joints other than the given one of the arm joints. In some such embodiments, the restricting can be by disabling actuation of arm joints of the arm other the given one of the arm joints.

In some embodiments, the user-input device can be effective to control the actuation of the plurality of arm joints in both the retroflexing mode and the surgical-operation mode.

In some embodiments, the surgical system can be configured such that the user-input device can be precluded from generating or transmitting control outputs that would control actuation of arm joints of the arm other than the given one of the arm joints.

In some embodiments, the surgical system can be configured such that the transitioning to the surgical-operation mode can be in response to and/or contingent upon detecting that the arm is in a retroflex position.

In some embodiments, the surgical system can be configured such that the transitioning can includes calibrating the user-input device with respect to at least one of a position and an orientation of the end effector or of a distal portion of the arm.

In some embodiments, the surgical system can be additionally configured to effect unflexing the distal end of the arm, following the operating in the second mode, so as to bring the arm to an unflexed position.

A method is disclosed, according to embodiments, of operating a surgical system comprising (i) an articulated mechanical arm comprising a surgical end effector at a distal end thereof and a plurality of arm joints and (ii) an input-device array of one or more user-input devices, wherein the arm joints are configured to flex and rotate in response to an electronic control-output from one or more user-input devices of the input-device array. The method comprises: (a) commencing operation of the surgical system in a first operating mode defined with respect to a given single one of the arm joints, wherein the first operating mode precludes actuation of any arm joint of the arm that is not the given single arm joint, and permits controlling the actuation of the single arm joint to cause a flexion of and a rotation of the single arm joint; (b) while the surgical system is in the first operating mode, (i) retroflexing the distal end of the arm by flexion and rotation of the single arm joint, in response to control signals generated by one or more of the user-input devices of the input-device array, so as to bring the end effector to a retroflex operating position, and (ii) monitoring a status of the mechanical arm to detect whether or not the arm is in a retroflex position. The method additionally comprises: (c) in response to and contingent upon detecting that the arm is in a retroflex position, transitioning operation of the surgical system from the first operating mode to a second operating mode in which the system is enabled to control flexing and rotating of at least one first-mode-precluded arm joint in accordance with respective degrees of freedom of each arm joint; and (d) operating the surgical system in the second operating mode so as to perform a surgical action using the end effector.

In some embodiments, the surgical system can additionally comprise control circuitry effective, while the surgical system is in the first operating mode, to restrict the actuation of arm joints other than the single arm joint. In some such methods, the restricting can be by disabling actuation of arm joints of the arm other the single arm joint. In some such embodiments, the input device can be precluded from generating or transmitting control outputs that would control actuation of arm joints of the arm other than the single arm joint. In some such embodiments, the restricting can include disabling a capability of the first input device. In some such embodiments, it can be that (i) a first input device of the input-device array controls actuation of the single arm joint while the surgical system is in the first operating mode, and a second input device controls actuation of the plurality of arm joints while the surgical system is in the second operating mode and/or (ii) the restricting is by providing a first input device that is configured for controlling actuation of the single arm joint and that is not configured for controlling actuation of arm joints other than the single arm joint.

In some embodiments, the transitioning can include calibrating the input device with respect to at least one of a position and an orientation of the end effector or of a distal portion of the arm.

In some embodiments, it can be that a first input device of the input-device array controls actuation of the single arm joint while the surgical system is in the first operating mode, and/or that a second input device of the input-device array controls actuation of the plurality of arm joints while the surgical system is in the second operating mode.

In some embodiments, the transitioning can include calibrating the second input device with respect to at least one of a position and an orientation of the end effector or of a distal portion of the arm.

In some embodiments, a single user-input device can control the actuation of the plurality of arm joints in both the first operating mode and the second operating mode.

In some embodiments of the method, the surgical system can additionally comprise a control console including a display screen, and at least one user-input device of the input-device array is disposed on or in proximity to the display screen.

In some embodiments, an additional user-input device for actuating linear advancement and retraction of the arm can be disposed upon, co-located with, or in proximity to, at least one user-input device of the input-device array.

In some embodiments, the retroflex operating position can be at, or in proximity to, a surgical worksite.

In some embodiments, the operating in the second mode can be with the arm in the retroflex position.

In some embodiments, the method can additionally comprise, following the operating in the second mode: unflexing the distal end of the arm, so as to bring the arm to an unflexed position.

According to embodiments, a surgical system for use with a surgical end effector and configured to operate, asynchronously, in a first operating mode and a second operating mode, comprises: (a) an input-device array of one or more user-input devices; and (b) an articulated mechanical arm comprising a surgical end effector at the distal end thereof, and a plurality of arm joints configured to flex and rotate in response to a control signal generated by one or more input devices of the input-device array, wherein: (i) the first operating mode is defined with respect to a given single one of the arm joints, wherein the first operating mode precludes actuation of any arm joint of the arm that is not the given single arm joint, and permits controlling the actuation of the single arm joint to cause a flexion and a rotation of the single arm joint, (ii) the system is configured to retroflex the distal end of the arm while in the first operating mode by actuating the single arm joint to cause a flexion of and a rotation of the single arm joint, in response to an electronic control-output from one or more of the user-input devices of the input-device array, so as to bring the surgical end effector to a retroflex operating position, (iii) the second operating mode is defined with respect to the plurality of arm joints, wherein the second operating mode enables controlling the actuation of at least one of the first-mode-precluded arm joints in accordance with respective degrees of freedom of each arm joint, and (iv) the system is configured to transition from the first operating mode to the second operating mode in response to and contingent upon a detection that the arm is in a retroflex position, and, while in the second operating mode, perform a surgical action using the end effector.

In some embodiments, the surgical system can additionally comprise control circuitry effective, while the surgical system is in the first operating mode, to restrict the actuation of arm joints other than the single arm joint. In some such embodiments, the restricting can be by disabling actuation of arm joints of the arm other the single arm joint. In some such embodiments, the input device can be precluded from generating or transmitting control outputs that would control actuation of arm joints of the arm other than the single arm joint. In some such embodiments, the restricting can include disabling a capability of the first input device. In some such embodiments, it can be that (i) a first input device of the input-device array controls actuation of the single arm joint while the surgical system is in the first operating mode, and a second input device controls actuation of the plurality of arm joints while the surgical system is in the second operating mode and/or (ii) the restricting is by providing a first input device that is configured for controlling actuation of the single arm joint and that is not configured for controlling actuation of arm joints other than the single arm joint.

In some embodiments, the system can be configured such that the transitioning can include calibrating the input device with respect to at least one of a position and an orientation of the end effector or of a distal portion of the arm.

In some embodiments, it can be that a first input device of the input-device array is effective to control actuation of the single arm joint while the surgical system is in the first operating mode, and/or that a second input device of the input-device array is effective to control actuation of the plurality of arm joints while the surgical system is in the second operating mode.

In some embodiments, the system can be configured such that the transitioning can include calibrating the second input device with respect to at least one of a position and an orientation of the end effector or of a distal portion of the arm.

In some embodiments, a single user-input device can be effective to control the actuation of the plurality of arm joints in both the first operating mode and the second operating mode.

In some embodiments, the surgical system can additionally comprise a control console including a display screen, and at least one user-input device of the input-device array is disposed on or in proximity to the display screen.

In some embodiments, an additional user-input device for actuating linear advancement and retraction of the arm can be disposed upon, co-located with, or in proximity to, at least one user-input device of the input-device array.

In some embodiments, the retroflex operating position can be at, or in proximity to, a surgical worksite.

In some embodiments, the operating in the second mode can be with the arm in the retroflex position.

In some embodiments, the surgical system can be additionally configured to effect unflexing the distal end of the arm, following the operating in the second mode, so as to bring the arm to an unflexed position. A method is disclosed, according to embodiments, of operating a surgical system that comprises (i) an articulated mechanical arm comprising a plurality of arm joints, and a surgical end effector at a distal end of the arm, and (ii) an input-device array of one or more user-input devices for controlling the arm. The method comprises: (a) retroflecting a distal portion of the articulated mechanical arm by flexion and rotation of a given one of arm joints, responsive to electronic control-output from the input-device array, so as to bring the end effector to a retroflex operating position without flexing or rotating any of the arm joints other than the given one of the arm joints; and (b) in response to and contingent upon detecting that the arm is in a retroflex position, effect flexing and rotating of at least two of the arm joints in accordance with respective degrees of freedom of each arm joint, responsive to electronic control-output from the input-device array, to thereby move the surgical end-effector to perform one or more surgical actions.

In some embodiments of the method, the surgical system can additionally comprise control circuitry effective to restrict the actuation of arm joints other than the given one of the arm joints during the retroflexing.

In some embodiments, the method can additionally comprise, following the performing the one or more surgical actions, unflexing the distal end of the arm, so as to bring the arm to an unflexed position.

According to embodiments, a surgical system comprises: (a) an articulated mechanical arm comprising (i) a plurality of arm joints and (ii) a surgical end effector at a distal end of the arm, and (b) an input-device array of one or more user-input devices for controlling the arm, wherein the surgical system is configured: (i) to retroflect a distal portion of the articulated mechanical arm by flexion and rotation of a given one of arm joints, responsive to electronic control-output from the input-device array, so as to bring the end effector to a retroflex operating position without flexing or rotating any of the arm joints other than the given one of the arm joints, and (ii) to effect flexing and rotating of at least two of the arm joints in accordance with respective degrees of freedom of each arm joint in response to and contingent upon detecting that the arm is in a retroflex position, and responsively to electronic control-output from the input-device array, to thereby move the surgical end-effector to perform one or more surgical actions.

In some embodiments, the surgical system can additionally comprise control circuitry effective to restrict the actuation of arm joints other than the given one of the arm joints during the retroflexing.

In some embodiments of the method, the surgical system can additionally comprise control circuitry effective to restrict the actuation of arm joints other than the given one of the arm joints during the retroflexing.

In some embodiments, the method can additionally comprise, following the performing the one or more surgical actions, unflexing the distal end of the arm, so as to bring the arm to an unflexed position.

A method is disclosed, according to embodiments, of using a surgical system. The method comprises: (a) providing an articulated mechanical arm having a surgical end effector at a distal end thereof, the arm comprising a plurality of arm segments connected serially by a corresponding plurality of arm joints configured to flex and rotate in response to an electronic control-output from a user-input device, wherein the providing is such that the end effector is displaced; (b) maneuvering the end effector to a retroflex operating position while operating in a first input mode in which a displacement of an input device or of a displaceable portion thereof is translated to a speed of at least one of (i) a flexion of an arm joint and (ii) a rotation of an arm joint; (c) in response to and contingent upon detecting that the end effector is in the retroflex operating position, transitioning from operating in the first input mode to operating in a second input mode in which a displacement of an input device or of a displaceable portion thereof is translated to a corresponding displacement of at least one arm segment; and (d) after the transitioning and while operating in the second input mode, performing a surgical action using the end effector.

In some embodiments, a single user-input device can be used in both the first input mode and the second input mode.

In some embodiments, it can be that a first input device is used in the first input mode, and/or that a second input device is used in the second input mode.

In some embodiments, an additional user-input device can be used for actuating linear advancement and retraction of the arm.

In some embodiments, the retroflex operating position can be at, or in proximity to, a surgical worksite.

According to embodiments, a surgical system for use with a surgical end effector comprises: (a) an articulated mechanical arm having a surgical end effector at a distal end thereof, the arm comprising a plurality of arm segments connected serially by a corresponding plurality of arm joints configured to flex and rotate in response to an electronic control-output from a user-input device; and (b) an array of one or more input devices for controlling the arm, wherein the surgical system is configured: (i) to operate, asynchronously, in (A) a first input mode in which a displacement of an input device or of a displaceable portion thereof is translated to a speed of a flexion and of a rotation of an arm joint, and in (B) a second input mode in which a displacement of an input device or of a displaceable portion thereof is translated to a corresponding displacement of at least one arm segment; (ii) while operating in the first input mode, to maneuver the end effector to a retroflex operating position during a first stage in which the end effector is displaced; and (iii) while operating in the second input mode, to perform a surgical action using the end effector.

In some embodiments, the system can be configured such that a single user-input device can be used in both the first input mode and the second input mode.

In some embodiments, the system can be configured such that a first input device is used in the first input mode, and/or that a second input device is used in the second input mode.

In some embodiments, the system can be configured such that an additional user-input device can be used for actuating linear advancement and retraction of the arm.

In some embodiments, the retroflex operating position can be at, or in proximity to, a surgical worksite.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons skilled in the art to which the invention pertains.

Any feature or combination of features described in the present document may be combined with any feature or combination of features described in U.S. patent application Ser. No. 16/377,280 filed on Apr. 8, 2019 and published as US Patent Publication US201902314445; U.S. patent application Ser. No. 15/915,237 filed on Mar. 8, 2018 and published as US Patent Publication US20180256246A1; and U.S. patent application Ser. No. 15/454,123 filed on Mar. 9, 2017 and published as US Patent Publication US20170258539A1; U.S. patent application Ser. No. 15/501,862 filed on Feb. 6, 2017 and published as US Patent Publication US20170239005A1; all of which are hereby incorporated by reference herein as if fully set forth in their entirety.

In the description and claims of the present disclosure, each of the verbs, "comprise", "include" and "have", and conjugates thereof, are used to indicate that the object or objects of the verb are not necessarily a complete listing of members, components, elements or parts of the subject or subjects of the verb. As used herein, the singular form "a", "an" and "the" include plural references unless the context clearly dictates otherwise. For example, the term "a marking" or "at least one marking" may include a plurality of markings.

The invention claimed is:

1. A method of operating a surgical system that comprises (i) an articulated mechanical arm having a surgical end effector at a distal end thereof, the arm comprising a plurality of arm joints having respective degrees of freedom, and (ii) an input-device array of one or more user-input devices configured to control flexing and rotating of arm joints, the method comprising:
   a. in response to an electronic control-output from a first user-input device, retroflecting the distal end of the arm so as to deliver the end effector to a retroflex operating position, employing a first coordinate translation matrix defining a first x-y-z space to translate a user-input to a respective flexion and rotation of an arm joint;
   b. in response to and contingent upon detecting that the end effector is in the retroflex operating position, transitioning to a second coordinate translation matrix defining a second x-y-z space that is based on the retroflex position of the end effector; and
   c. after the transitioning and in response to an electronic control-output from a second user-input device, performing a surgical activity using the end effector, employing the second coordinate translation matrix to translate a user-input to a respective flexion and rotation of an arm joint.

2. The method of claim 1, wherein the first and second input devices are the same input device, and the first and second coordinate translation matrices are not the same 3D-coordinate translation matrix.

3. The method of claim 1, wherein the first and second input devices are not the same input device, and the first and second coordinate translation matrices are not the same 3D-coordinate translation matrix.

4. The method claim 1, wherein before the transition and during the retroflecting, a proximal displacement of the first user-input device or a part thereof is translated to a proximal displacement of the end effector, and after the transition and with the end effector in the retroflex position, a proximal displacement of the second user-input device or a part thereof is translated to a distal displacement of the end effector.

5. The method of claim 1, wherein the first input device is deactivated after the transition.

6. The method of claim 1, wherein the second input-device comprises a handle member configured to be oriented in any one of a plurality of selectable orientations in an x-y-z space, the handle member comprising respective segment members and joint members that correspond, respectively, to the arm segments and arm joints of the arm, each of the respective arm joints actuatable by, and having the same degrees of freedom as, the corresponding joint member.

7. The method of claim 6, wherein performing the surgical activity using the end effector includes reorienting the handle member to displace and reorient, respectively, the segment members and joint members, thereby causing respective displacement and reorientation of the corresponding arm segments and arm joints of the retroflected arm, the orientation of the handle member being such that a displacement vector or a reorientation arc of the handle member through the x-y-z space is translated to a corresponding displacement vector or corresponding reorientation arc of the end effector in the same x-y-z space.

8. The method of claim 6, wherein the retroflecting in response to the electronic control-output from the first input device does not include reorienting the handle member from a selected orientation in the x-y-z space.

9. The method of claim 6, wherein the retroflecting in response to the electronic control-output from the first input device does not include reorienting the handle member from a selected orientation in the x-y-z space by more than 90°.

10. The method of claim 1, wherein the first input-device is disconnected from the arm after the transitioning.

11. The method of claim 1, wherein
 i. detecting that the end effector is in the retroflex operating position includes monitoring a shape-status of said mechanical arm to detect whether at least a portion thereof has a curve-shape that matches a pre-defined curve-shape, and
 ii. the transitioning to the second coordinate translation matrix is in response to and contingent upon detecting that the curve-shape of the mechanical arm matches the pre-defined curve-shape.

12. The method of claim 11, wherein detecting whether the curve-shape of the mechanical arm or of a portion thereof matches the pre-defined curve shape includes at least one of (i) detecting whether the curve-shape of the mechanical arm or a portion thereof matches a two-dimensional projection of the pre-defined curve shape, (ii) detecting whether a two-dimensional projection of the curve-shape of the mechanical arm or of a portion thereof matches the pre-defined curve-shape, and (iii) detecting whether a two-dimensional projection of the curve shape of the mechanical arm or of a portion thereof matches a two-dimensional projection of the pre-defined curve shape.

13. The method of claim 11, wherein the pre-defined curve-shape or a two-dimensional projection thereof is an "S" curve-shape.

14. A surgical system for use with a surgical end effector, the system comprising:
 a. an array of one or more input devices; and
 b. an articulated mechanical arm having a surgical end effector at a distal end thereof, the arm comprising a plurality of arm segments connected by a plurality of arm joints configured to flex and rotate in response to a control signal generated by an input device,
 wherein the surgical system is configured to:
  i. retroflect the distal end of the arm, in response to an electronic control-output from a first user-input device, so as to deliver the end effector to a retroflex operating position, employing a first coordinate translation matrix defining a first X-y-z space to translate the user inputs to respective flexions and rotations of an arm joint,
  ii. transition to a second coordinate translation matrix that is based on a current orientation of the end effector, in response to and contingent upon a detection that said current orientation of the end effector corresponds to a current orientation of a second user-input device, and
  iii. perform a surgical activity using the end effector after the transitioning and in response to an electronic control-output from the second user-input device, employing the second coordinate translation matrix defining a second x-y-z space to translate the user-inputs to respective flexions and rotation of an arm joint.

* * * * *